US012797068B2

(12) United States Patent
Marriott et al.

(10) Patent No.: US 12,797,068 B2
(45) Date of Patent: Nov. 17, 2026

(54) SYSTEMS AND SUBSYSTEMS FOR OPERATING AN END EFFECTOR OF A SURGICAL INSTRUMENT

(71) Applicant: CILAG GMBH INTERNATIONAL, Zug (CH)

(72) Inventors: Douglas Marriott, Cincinnati, OH (US); Joseph Mozloom, Jr., Cincinnati, OH (US); Jeffrey Franklin, Cincinnati, OH (US); Zachary Miller, Cincinnati, OH (US); Darryl A. Parks, Cincinnati, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 0 days.

(21) Appl. No.: 18/775,380

(22) Filed: Jul. 17, 2024

(65) Prior Publication Data

US 2024/0366221 A1 Nov. 7, 2024

Related U.S. Application Data

(60) Provisional application No. 63/640,289, filed on Apr. 30, 2024, provisional application No. 63/515,020, filed on Jul. 21, 2023.

(51) Int. Cl.
*A61B 17/072* (2006.01)
*A61B 34/30* (2016.01)

(52) U.S. Cl.
CPC ........ *A61B 17/07207* (2013.01); *A61B 34/30* (2016.02); *A61B 2017/07264* (2013.01);
(Continued)

(58) Field of Classification Search
CPC ............ A61B 17/07207; A61B 17/285; A61B 17/295; A61B 1027/291; A61B 2017/07214–07285
See application file for complete search history.

(56) References Cited

U.S. PATENT DOCUMENTS 7,691,098 B2 4/2010 Wallace et al.
8,827,134 B2 9/2014 Viola et al.
(Continued)

FOREIGN PATENT DOCUMENTS

AU 2014223723 B2 2/2015
CN 105682567 * 6/2016 ... A61B 2017/07257
(Continued)

OTHER PUBLICATIONS

International Search Report and Written Opinion mailed Oct. 16, 2024 in corresponding International Patent Application No. PCT/IB2024/056978.

*Primary Examiner* — Linda J. Hodge
*Assistant Examiner* — Anna Kinsaul
(74) *Attorney, Agent, or Firm* — Troutman Pepper Locke LLP

(57) ABSTRACT

A surgical instrument designed to operate with a robotic platform is disclosed. The surgical instrument assembly includes a shaft, an end effector, a knife firing subsystem to actuate functions of the end effector, an articulation subsystem that is actuatable to articulate the end effector, an articulation joint about which the end effector articulates, a roll subsystem to roll the shaft, and a housing that couples to the robotic platform. The end effector includes a jaw. The end effector includes an anvil coupled to the jaw and movable between an open position, a grasping position, and a clamping position. The end effector includes a knife slidably coupled to the anvil to move the anvil between the open position, the grasping position, and the clamping position.

19 Claims, 40 Drawing Sheets

(52) U.S. Cl.
CPC ............... *A61B 2017/07271* (2013.01); *A61B 2017/07278* (2013.01); *A61B 2017/07285* (2013.01)

(56) References Cited

U.S. PATENT DOCUMENTS

| | | | |
|---|---|---|---|
| 9,289,208 | B1 | 3/2016 | Knodel et al. |
| 9,642,620 | B2 | 5/2017 | Baxter, III et al. |
| 10,478,185 | B2 | 11/2019 | Nicholas et al. |
| 11,154,299 | B2 | 10/2021 | Shelton, IV et al. |
| 11,197,672 | B2 | 12/2021 | Dunki-Jacobs et al. |
| 11,278,279 | B2 | 3/2022 | Morgan et al. |
| 11,813,746 | B2 | 11/2023 | Overmyer et al. |
| 12,178,536 | B2 | 12/2024 | Overmyer et al. |
| 12,279,768 | B2 | 4/2025 | Witte |
| 2011/0248064 | A1 | 10/2011 | Marczyk et al. |
| 2011/0290854 | A1 | 12/2011 | Timm et al. |
| 2012/0205421 | A1 | 8/2012 | Shelton, IV et al. |
| 2013/0274722 | A1 | 10/2013 | Kostrzewski et al. |
| 2014/0276722 | A1 | 9/2014 | Parihar et al. |
| 2014/0276931 | A1 | 9/2014 | Parihar et al. |
| 2014/0303646 | A1 | 10/2014 | Morgan et al. |
| 2015/0173755 | A1 | 6/2015 | Baxter, III et al. |
| 2015/0230796 | A1 | 8/2015 | Calderoni et al. |
| 2015/0374396 | A1* | 12/2015 | Strobl ................ A61B 18/1445 606/207 |
| 2017/0319205 | A1 | 11/2017 | Beardsley |
| 2018/0008265 | A1* | 1/2018 | Hatanaka ........... A61B 17/0682 |
| 2018/0168596 | A1 | 6/2018 | Beckman et al. |
| 2018/0353178 | A1 | 12/2018 | Shelton, IV et al. |
| 2019/0059986 | A1 | 2/2019 | Shelton, IV |
| 2019/0099181 | A1 | 4/2019 | Shelton, IV et al. |
| 2019/0183594 | A1 | 6/2019 | Shelton, IV et al. |
| 2019/0239967 | A1 | 8/2019 | Ragosta et al. |
| 2020/0138463 | A1 | 5/2020 | Kostrzewski et al. |
| 2020/0397433 | A1* | 12/2020 | Lytle, IV ......... A61B 17/07207 |
| 2021/0059773 | A1 | 3/2021 | Overmyer et al. |
| 2021/0186494 | A1 | 6/2021 | Shelton, IV et al. |
| 2021/0267596 | A1 | 9/2021 | Fanelli et al. |
| 2022/0008070 | A1 | 1/2022 | Fremd |
| 2022/0031320 | A1 | 2/2022 | Hall et al. |
| 2022/0031322 | A1* | 2/2022 | Parks ..................... A61B 34/30 |
| 2022/0031323 | A1 | 2/2022 | Witte |
| 2022/0031345 | A1 | 2/2022 | Witte et al. |
| 2022/0071632 | A1* | 3/2022 | Patel ................ A61B 17/07207 |
| 2022/0218350 | A1 | 7/2022 | Shelton, IV et al. |
| 2022/0240928 | A1 | 8/2022 | Timm et al. |
| 2022/0304679 | A1 | 9/2022 | Bakos et al. |
| 2022/0346790 | A1* | 11/2022 | Wellman .......... A61B 17/07207 |
| 2022/0378424 | A1 | 12/2022 | Huang et al. |
| 2023/0051222 | A1 | 2/2023 | Shelton, IV et al. |
| 2023/0120209 | A1 | 4/2023 | Parks et al. |
| 2023/0210527 | A1 | 7/2023 | Shelton, IV et al. |
| 2024/0366221 | A1 | 11/2024 | Marriott et al. |
| 2025/0120700 | A1 | 4/2025 | Fiebig et al. |

FOREIGN PATENT DOCUMENTS

| | | | | | |
|---|---|---|---|---|---|
| EP | 2737922 | A1 | | 6/2014 | |
| EP | 3501412 | A2 | | 6/2019 | |
| EP | 3235445 | B1 | | 4/2022 | |
| EP | 3511413 | B1 | | 7/2022 | |
| WO | WO-9424947 | A1 | * | 11/1994 | ....... A61B 17/07207 |
| WO | 2013155155 | A2 | | 10/2013 | |
| WO | 2014158452 | A1 | | 10/2014 | |
| WO | WO-2018116013 | A1 | * | 6/2018 | ......... A61B 17/0682 |

* cited by examiner

SYSTEMS AND SUBSYSTEMS FOR OPERATING AN END EFFECTOR OF A SURGICAL INSTRUMENT

CROSS-REFERENCE TO RELATED APPLICATIONS

This application claims the benefit of and priority to U.S. Provisional Patent Application No. 63/515,020 filed Jul. 21, 2023 and U.S. Provisional Patent Application Ser. No. 63/640,289 filed Apr. 30, 2024, the disclosures of which are expressly incorporated herein by reference.

BACKGROUND

The present disclosure relates to surgical instruments and, in various arrangements, to surgical stapling and cutting instruments and staple cartridges for use therewith that are designed to staple and cut tissue.

SUMMARY

The disclosed technology can be for systems, devices, and subsystems for surgical instruments for robotic surgeries. The surgical instruments can have several subsystems that can be independently actuated to provide a specific action, such as closing and opening of an end effector of the stapler, articulation of the end effector, rolling of the end effector, and firing of staples within the end effector.

The disclosed technology describes an end effector, which can be one of a number of subsystems and/or subcomponents for a surgical instrument. The end effector includes a jaw. The end effector includes an anvil coupled to the jaw and movable between an open position, a grasping position, and a clamping position. The end effector includes a knife slidably coupled to the anvil to move the anvil between the open position, the grasping position, and the clamping position. The end effector can be combined with one or more of an articulation joint, articulation subsystem, firing subsystem, roll subsystem, and housing for implementation in the surgical instrument.

DETAILED DESCRIPTION

Figure 1:
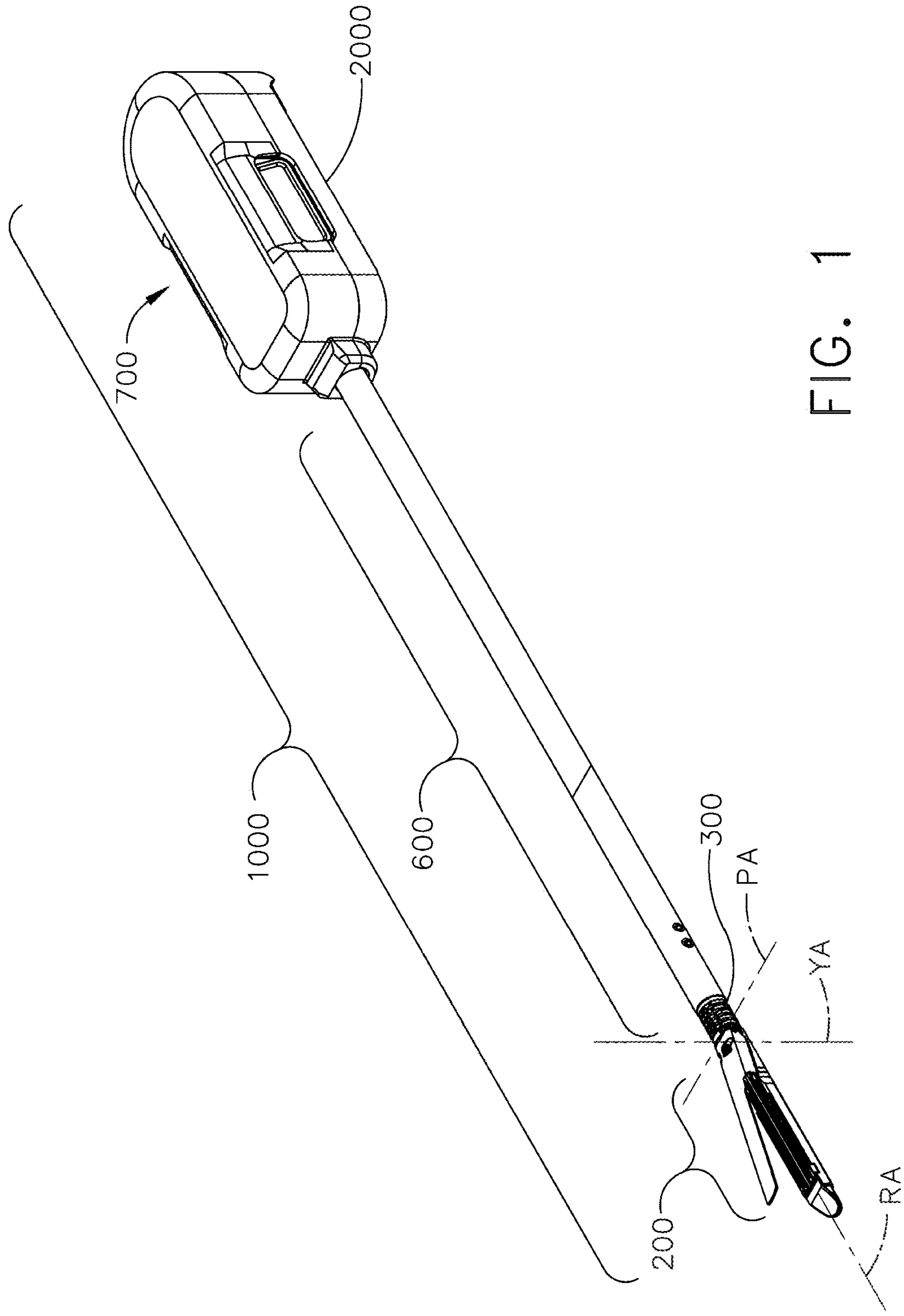
FIG. 1 is a schematic perspective view of a surgical system that includes a surgical instrument, in accordance with the disclosed technology.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a surgical system, device, or apparatus that "comprises," "has," "includes" or "contains" one or more elements possesses those one or more elements, but is not limited to possessing only those one or more elements. Likewise, an element of a system, device, or apparatus that "comprises," "has," "includes" or "contains" one or more features possesses those one or more features, but is not limited to possessing only those one or more features.

The terms "proximal" and "distal" are used herein with reference to a robotic platform manipulating the housing portion of the surgical instrument. The term "proximal" refers to the portion closest to the robotic platform and the term "distal" refers to the portion located away from the robotic platform. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Furthermore, the use of "couple", "coupled", or similar phrases should not be construed as being limited to a certain number of components or a particular order of components unless the context clearly dictates otherwise.

Also, where alternative examples of certain aspects of the surgical instrument are described, in instances where the same reference numbers as that of previously described examples are used to label components in the alternative example(s), the structure and functionality of those components is the same unless otherwise noted.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

A surgical stapling system can comprise a shaft and an end effector extending from the shaft. The end effector comprises a first jaw and a second jaw. The first jaw comprises a staple cartridge. The staple cartridge is insertable into and removable from the first jaw; however, other embodiments are envisioned in which a staple cartridge is not removable from, or at least readily replaceable from, the first jaw. The second jaw comprises an anvil configured to deform staples ejected from the staple cartridge. The anvil is pivotable relative to the first jaw about a closure axis; however, other embodiments are envisioned in which the first jaw is pivotable relative to the second jaw. The surgical stapling system further comprises an articulation joint configured to permit the end effector to be rotated, or articulated, relative to the shaft. Other embodiments are envisioned which do not include an articulation joint. In other words, other elements described herein can be employed in embodiments where no articulation joint is provided without departing from the spirit and scope of the present disclosure. Similarly, the articulation joint can be employed in embodiments where other elements described herein are omitted.

I. Overview of the Surgical Instrument

Figure 2:
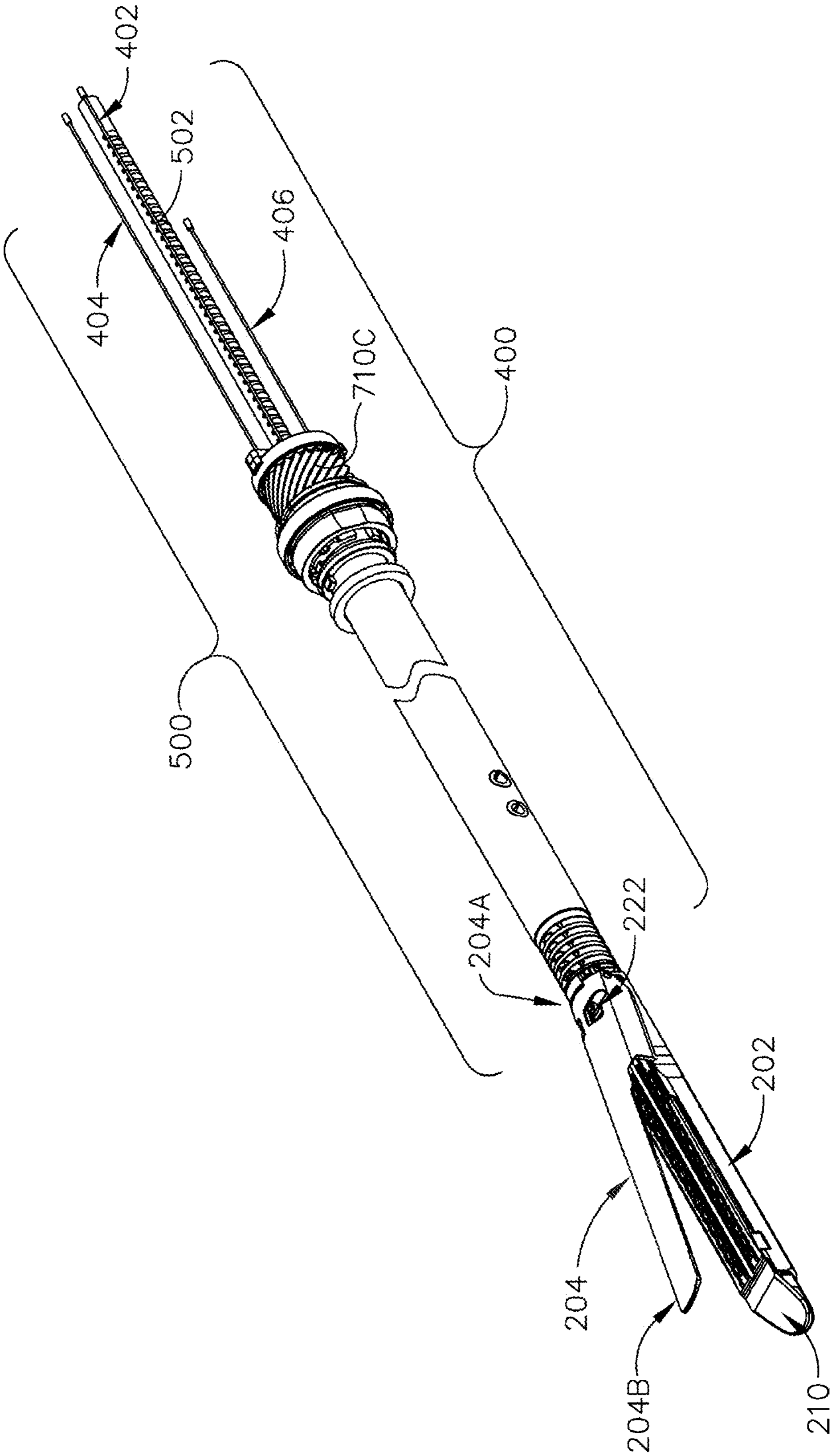
FIG. 2 is a schematic detail view of an end effector, articulation joint, and portions of a cable articulation subsystem, knife firing subsystem, and roll subsystem, in accordance with the disclosed technology.

A surgical instrument 1000 is illustrated in FIG. 1. As discussed in greater detail below, the surgical instrument 1000 is configured to grasp, clamp, incise, and seal patient tissue. The surgical instrument 1000 comprises an end effector 200, an articulation joint 300, an articulation drive subsystem 400 (FIG. 2) configured to articulate the end effector 200 about the articulation joint 300, a knife firing subsystem 500 (FIG. 2) configured to move the end effector between various positions (e.g., an open position, a grasping position, and a clamping position) and to incise and staple patient tissue, a roll subsystem 600 configured to roll the end effector 200 about a roll axis, and a housing 700.

II. Overview of the End Effector

Figure 3:
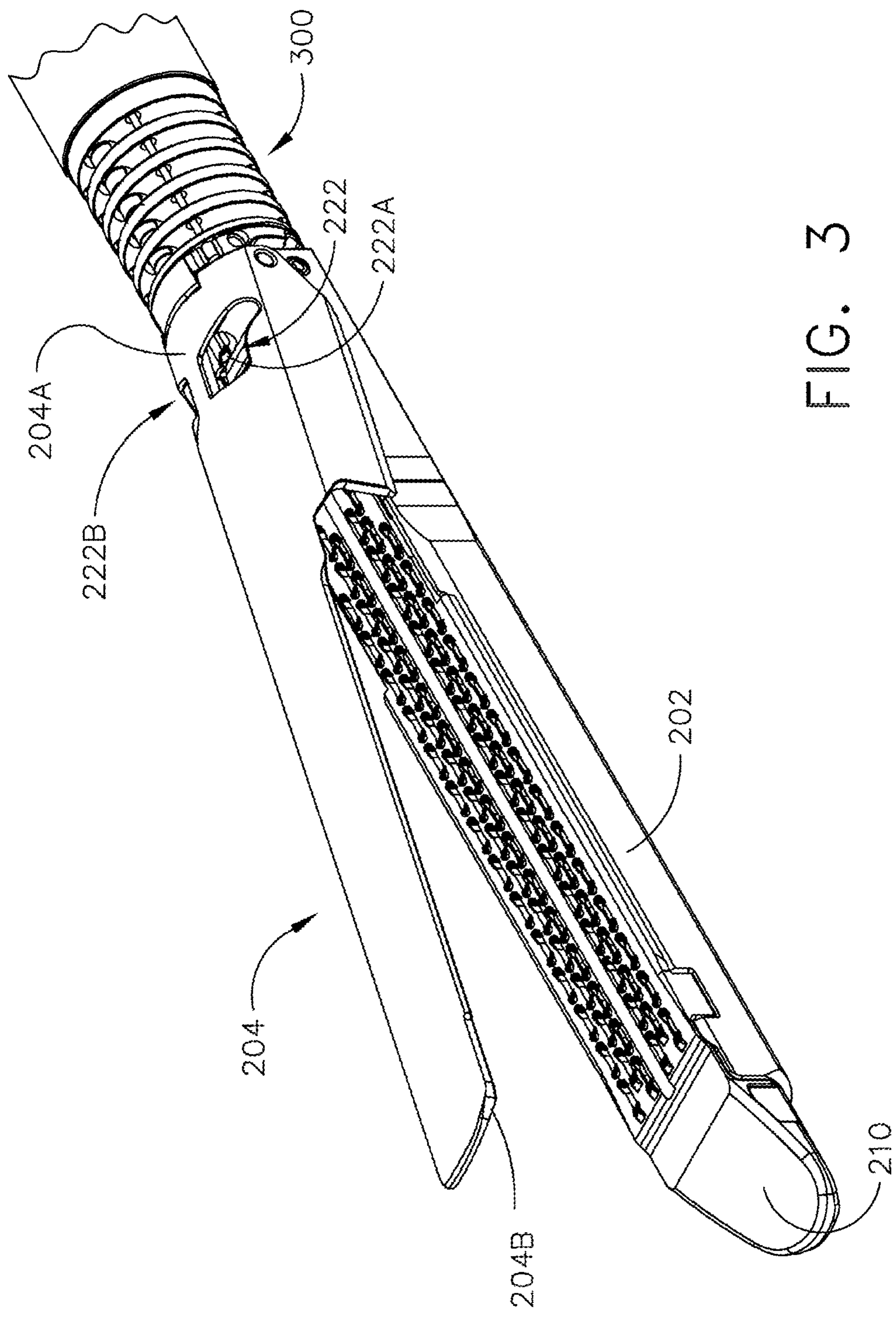
FIG. 3 is a schematic detail view of the end effector and the articulation joint, in accordance with the disclosed technology.
Figures 4, 5:
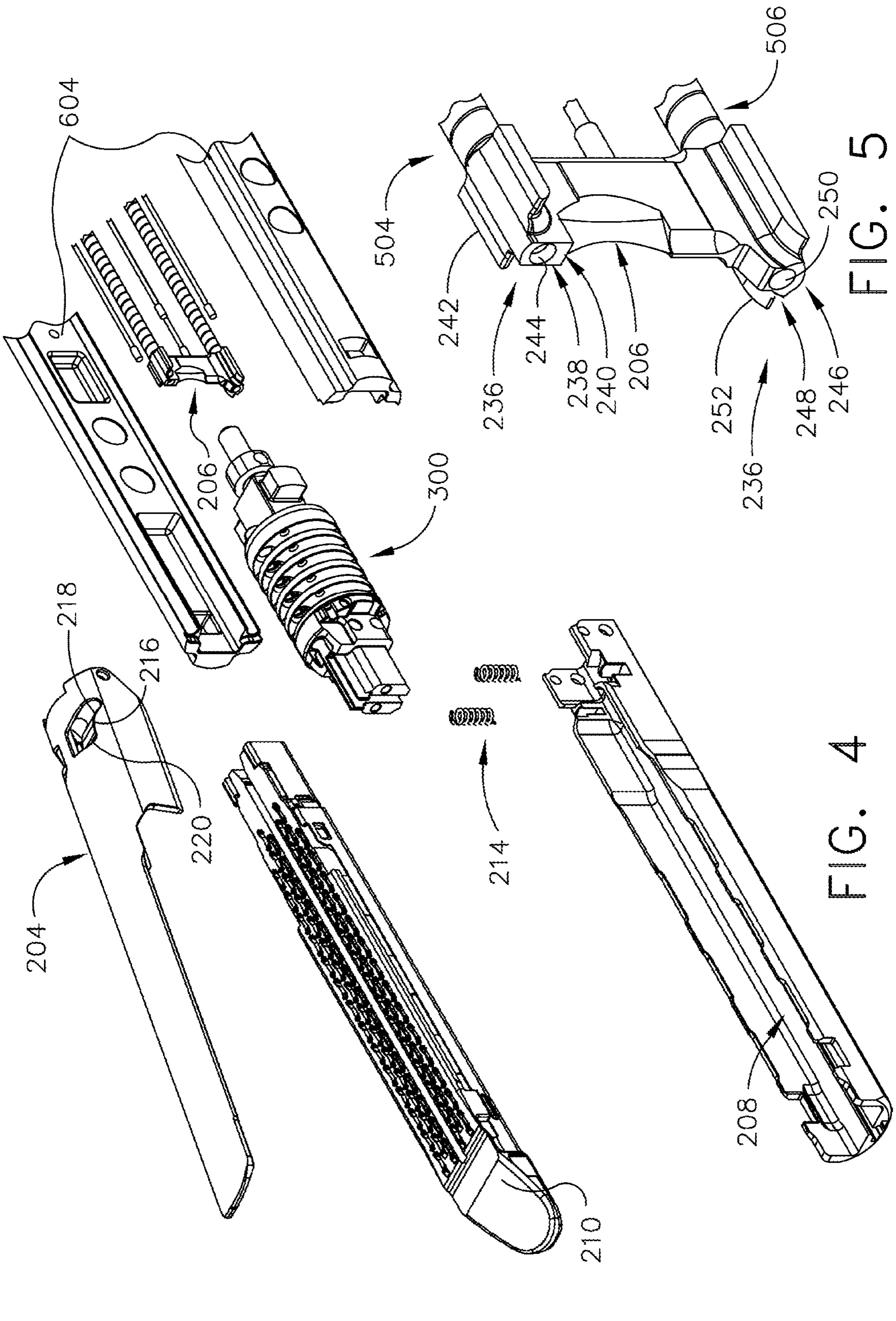
FIG. 4 is a schematic exploded view of a distal end of the surgical instrument, in accordance with the disclosed technology.
FIG. 5 is a schematic detail view of a knife, in accordance with the disclosed technology.
Figure 7:
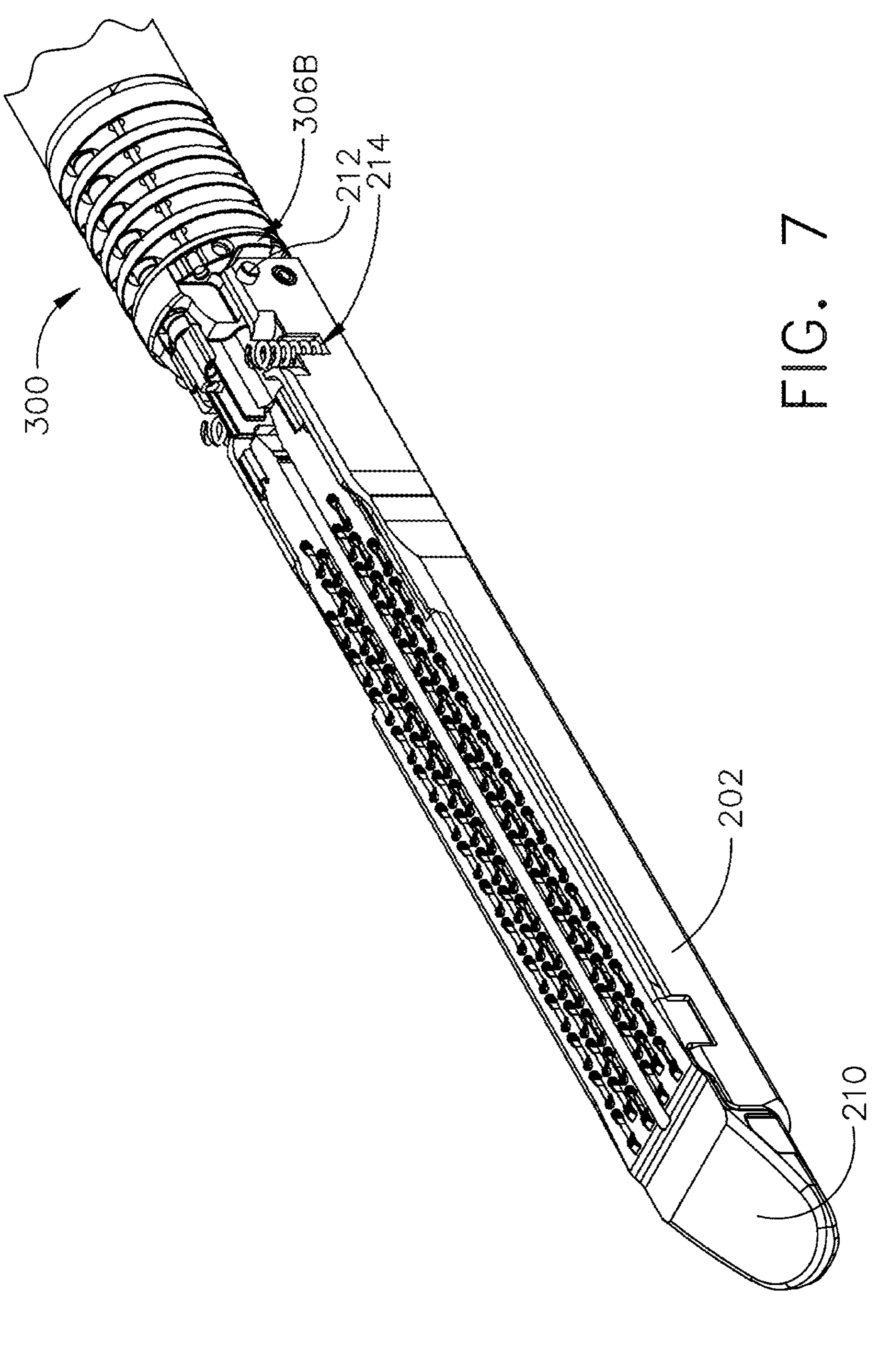
FIG. 7 is a schematic detail view of the end effector and the articulation joint, with an anvil of the end effector removed, in accordance with the disclosed technology.

The end effector 200 comprises a first jaw 202 and a second jaw 204 movable between an open position and a closed position. For clarity, first jaw 202 is herein also interchangeably used with "jaw 202" (which is also referred to in the art as a "channel") and second jaw 204 is used interchangeably with "anvil 204". The jaw 202 and anvil 204 may be elongated in form. The jaw 202 defines an elongated channel 208 for receiving a staple cartridge 210. The anvil 204 has a proximal end 204A, a distal end 204B, and a ramp surface 216 defined at the proximal end 204A, which is described in greater detail below with respect to FIGS. 4 and 9A-9D. The jaw 202 and anvil 204 are pivotally coupled via a pivot pin 212 that extends through the jaw 202 and the anvil 204. As seen in FIG. 7, one or more biasing springs 214 extend between the jaw 202 and anvil 204 to bias the anvil 204 to the open position. The ramp surface 216 may be visible via a kidney bean-shaped opening 222 (which may be formed as part of the manufacturing process to make the ramp surface 216) that has a first lateral end 216A and a second lateral end 216B. In other words, the kidney bean-shaped opening may be open at its lateral ends 222A, 222B (FIG. 3). As seen in FIG. 3, the ramp surface 216 forms a lower surface of the kidney bean-shaped opening 222. The ramp surface 216 can be arcuately shaped. For example, as shown particularly in FIGS. 4 and 9A-9D, it may be upwardly sloped at a first angle 218 and arcuately tapers, in a distal direction, to a substantially horizontal second angle 220. Ramp surface, by way of example, may include a single radius curve, a series of multi-radius curves, a series of multi-radius curves with a series of inflection points, and/or be linearly sloped.

Figure 8A:
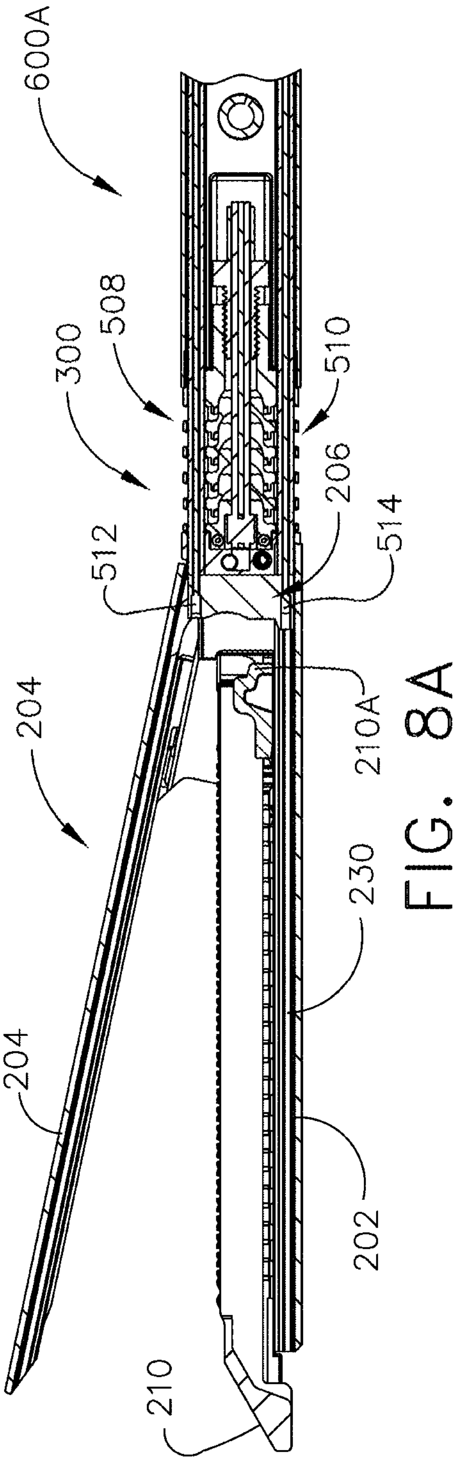
FIG. 8A is a schematic side cross-sectional view of the distal end of the surgical instrument, depicting the anvil in an open position, in accordance with the disclosed technology.

The anvil 204 further defines a longitudinally extending upper knife channel 224 (FIG. 8A, etc.). As shown particularly in FIG. 6, the upper knife channel 224 includes a centrally disposed cylindrical upper knife channel portion 226 and at least one lateral upper knife channel wing 228 that extends away from the upper knife channel portion 226. While the term 'cylindrical' is used, the channel portion 226 need not resemble a perfect cylinder.

II. 1. End Effector and Firing Subsystem

Figure 17:
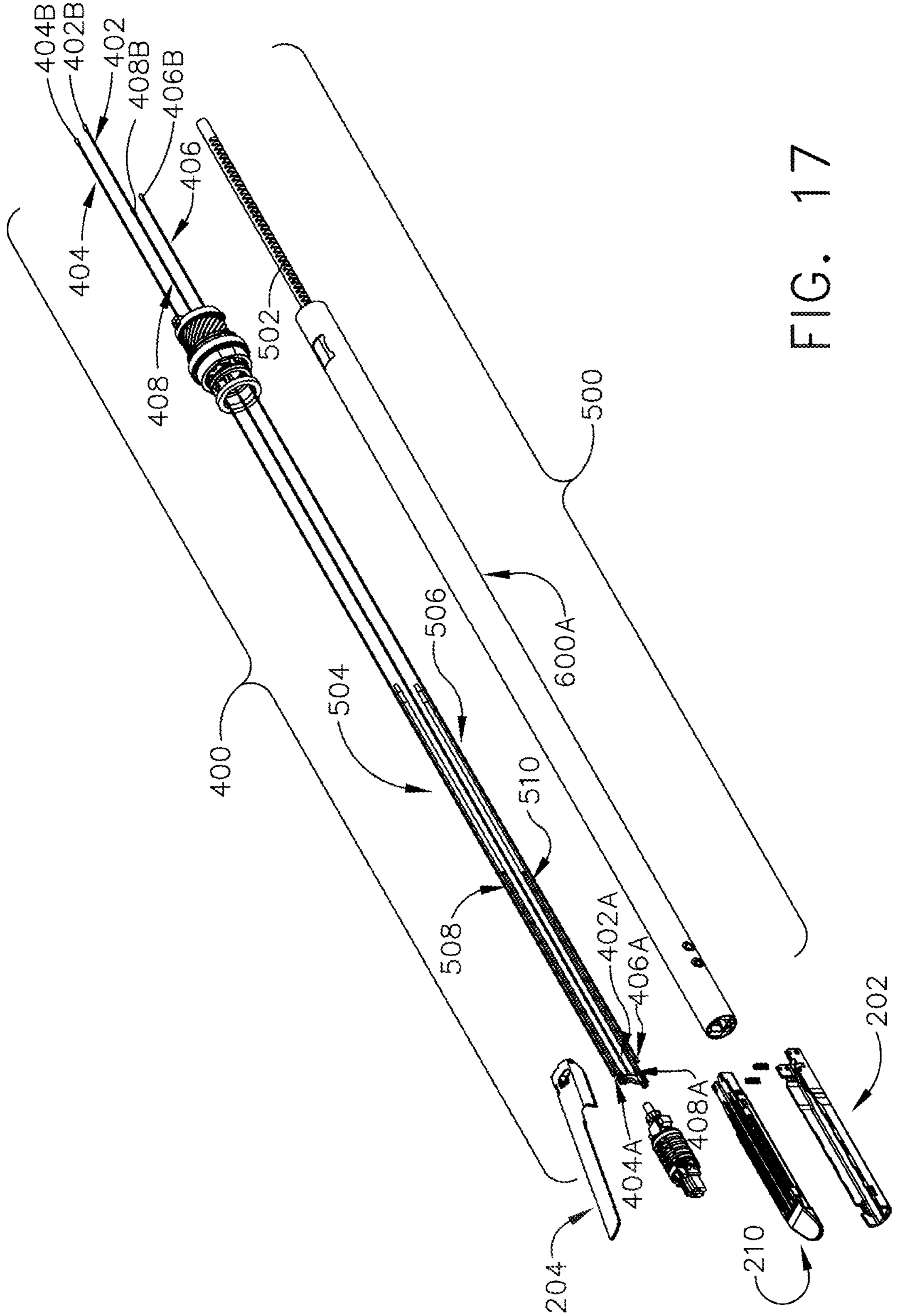
FIG. 17 is a schematic exploded view of the surgical instrument, depicting portions of the cable articulation subsystem, knife firing subsystem, and roll subsystem, in accordance with the disclosed technology.
Figure 18:
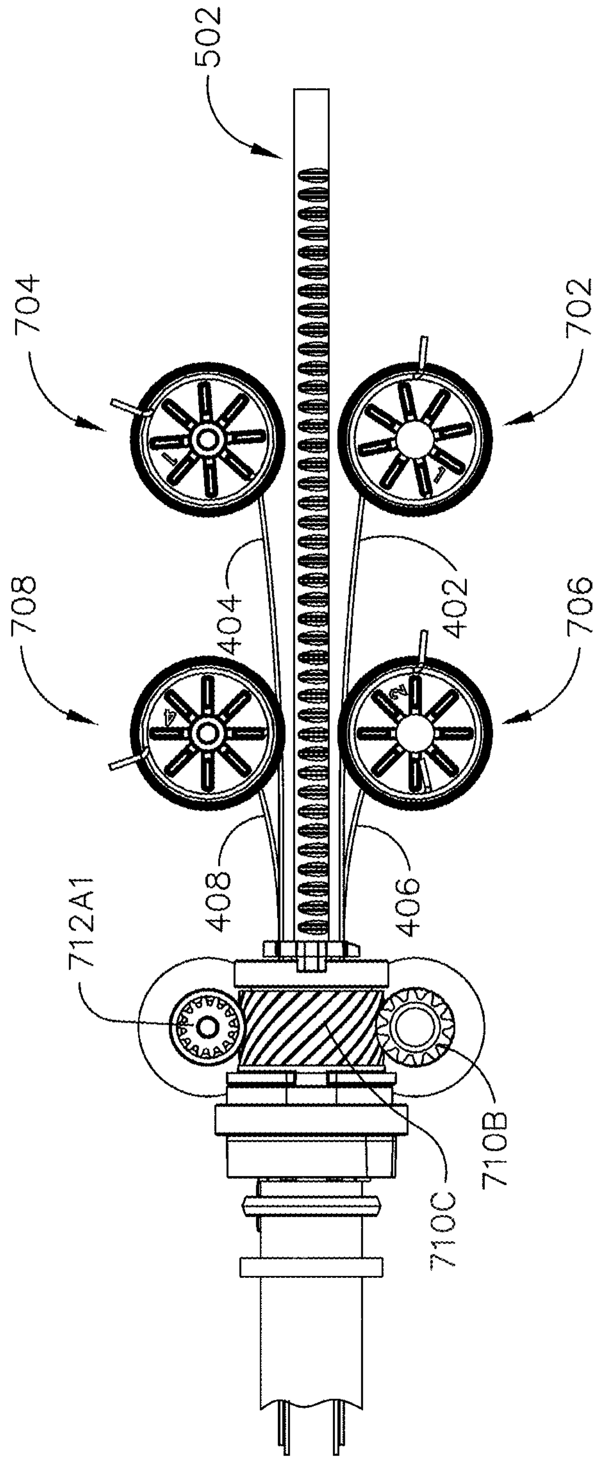
FIG. 18 is a schematic top view of a proximal end of the surgical instrument, depicting portions of the cable articulation subsystem, knife firing subsystem, and roll subsystem, in accordance with the disclosed technology.

The surgical instrument 1000 further comprises a knife firing subsystem 500 operable to close the anvil 204 during a closure stroke. After the end effector 200 is closed, the knife firing subsystem 500 (FIGS. 2 and 17) is operable to incise and staple, with staples from the staple cartridge 210, the patient tissue captured between the staple cartridge 210 (which is retained by the jaw 202) and anvil 204 during a firing stroke.

The knife firing subsystem 500, explained further below in greater detail, includes a knife 206. The knife 206 is coupled to or integral with a knife sled 236. The knife sled 236 is the non-cutting element of the knife 206, and is also referred to as an I-beam. The knife sled 236 includes an upper knife tab 238 and a lower knife tab 246. The upper knife tab 238 includes a centrally disposed cylindrical upper knife tab portion 240 and at least one upper knife tab lateral wing 242 that extends away from the upper knife tab portion 240. While the term 'cylindrical' is used, the tab portion need not resemble a perfect cylinder. In some embodiments, the upper knife tab 238 includes a pair of lateral wings 242 configured to slidably ride in the upper knife channel 224 to move the anvil 204 between the open position, the grasping position, and the clamping position. Each lateral wing 242 may include a ramped surface 242A that engages the anvil ramp surface 216. The upper knife tab portion 240 defines an upper knife tab opening 244 that is configured to receive a barrel crimp coupled to a center cable 512, which is described in greater detail below. The lower knife tab 246 includes a centrally disposed cylindrical lower knife tab portion 248 and at least one lower knife tab lateral wing 250 that extends away from the lower knife tab portion 248. While the term 'cylindrical' is used, the lower knife tab portion 248 need not resemble a perfect cylinder. In some embodiments, the lower knife tab 246 includes a pair of lateral wings 250. The lower knife tab portion 248 defines a lower knife tab opening 252 that is configured to receive a barrel crimp coupled to a center cable 514, which is described in greater detail below.

The staple cartridge 210 comprises a cartridge body. In use, the staple cartridge is positioned on a first side of the tissue to be stapled, within the channel 208 of the jaw 202, and the anvil 204 is positioned on a second side of the tissue. The anvil 204 is moved toward the staple cartridge 210 to compress and clamp the tissue against the deck of the staple cartridge 210. Thereafter, staples removably stored in the cartridge body can be deployed into the tissue. The cartridge body includes staple cavities defined therein wherein staples are removably stored in the staple cavities. In some embodiments, the staple cavities are arranged in six longitudinal rows. In some embodiments, three rows of staple cavities are positioned on a first side of a lower knife channel 230 and three rows of staple cavities are positioned on a second side of lower knife channel 230.

Figure 6:
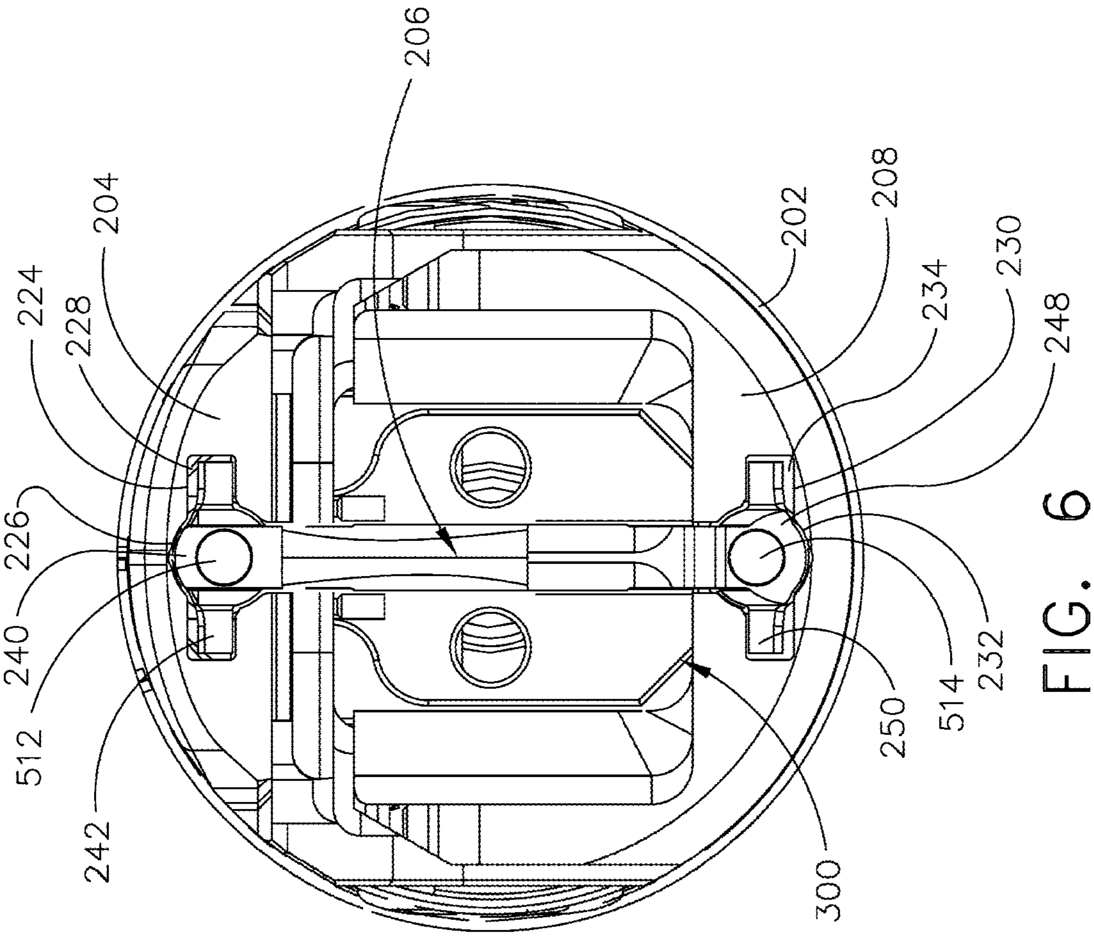
FIG. 6 is a schematic detail front view of the end effector, in accordance with the disclosed technology.

Making particular reference to FIG. 6, the lower knife channel 230 includes a centrally disposed cylindrical lower knife channel portion 232 and at least one lateral lower knife channel wing 234 that extends away from the lower knife channel portion 232. While the term 'cylindrical' is used, the channel portion 232 need not resemble a perfect cylinder. Other arrangements of staple cavities and staples may be possible. For example, in some embodiments, a lower knife channel 230 can be defined in the jaw 202.

Figure 8B:
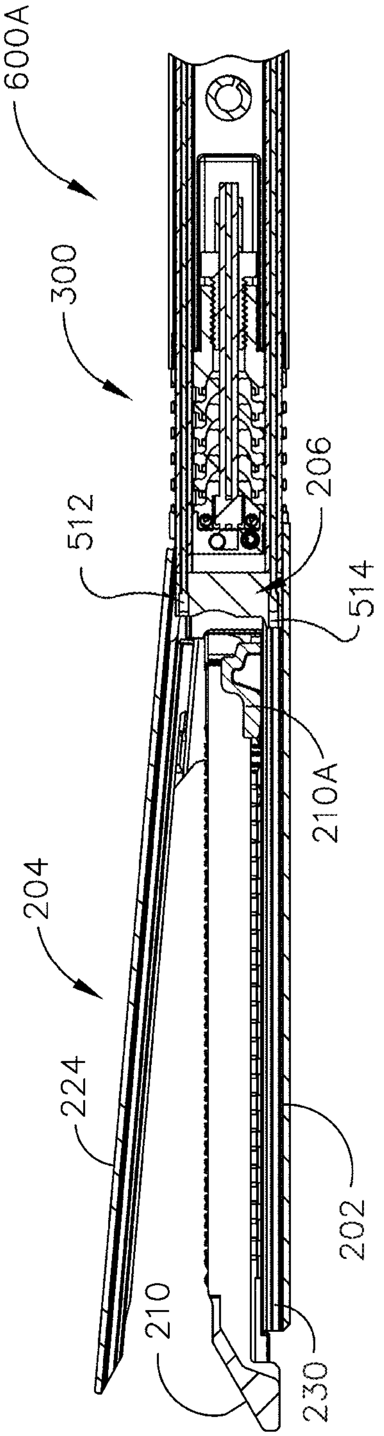
FIG. 8B is a schematic side cross-sectional view of the distal end of the surgical instrument, depicting the anvil in a grasping position with the knife partially advanced, in accordance with the disclosed technology.
Figure 8C:
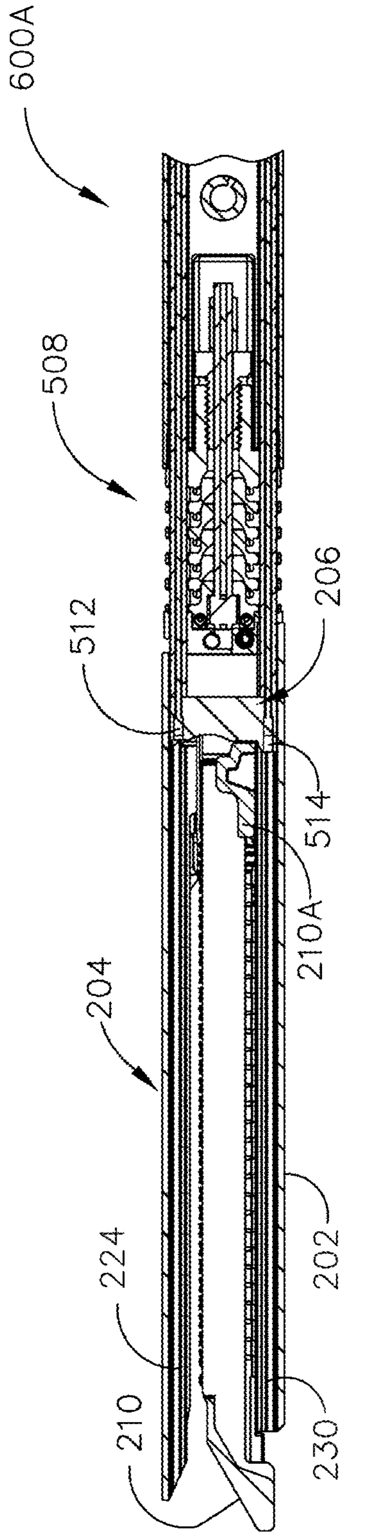
FIG. 8C is a schematic side cross-sectional view of the distal end of the surgical instrument, depicting the anvil in a clamping position with the knife partially advanced, in accordance with the disclosed technology.

The staples are supported by staple drivers in the cartridge body. The drivers are movable between a first, or unfired position, and a second, or fired, position to eject the staples from the staple cavities. The drivers are retained in the cartridge body by a retainer which extends around the bottom of the cartridge body and includes resilient members configured to grip the cartridge body and hold the retainer to the cartridge body. The drivers are movable between their unfired positions and their fired positions indirectly by the sled 236. More specifically, the knife sled 236 is movable between a proximal position adjacent the proximal end and a distal position adjacent the distal end. A portion of the knife sled 236 (e.g., see FIGS. 8C-8D) engages a cartridge sled 210A that slides under the drivers and lifts the drivers, and the staples supported thereon, toward the anvil 204. It is desirable for the knife 206 to be positioned at least partially proximal to the ramped surfaces such that the staples are in the second, or fired, position (i.e., ejected) ahead of the knife 206.

Further to the above, the sled 236 is moved distally and proximally by a firing rod 502. The firing rod 502 is configured to apply an indirect force to the sled 236, via push coils 508, 510 that directly engage the sled 236 (discussed in greater detail below) and push the sled 236 toward the distal end of the end effector 200. As the firing rod 502 is advanced distally, sled 236 rides in the lower knife channel 230 and the upper knife channel 224. At the onset of travel, the upper knife tab 238 rides along the anvil ramp surface 216. Specifically, as particularly seen in the sequence of FIGS. 8A-8D and 9A-9D, movement of the sled 236 distally causes the upper knife tab ramped surface 242A to slide along the anvil ramp surface 216. This movement first urges the anvil 204 closed to a position (e.g., FIGS. 8B and 9B) where a compressive force is applied to the tissue sufficient to grasp it (referred to as the grasping position). Continued movement of the sled 236 up the ramp surface 216 (e.g., see FIGS. 8C and 9C) results in a compressive force being applied to the tissue (referred to as the clamping position). As the anvil ramp surface 216 transitions to its substantially horizontally angled surface 218 (e.g., see FIGS. 8D and 9D), the upper knife tab 238 can slide within the upper knife channel 224 to drive the stapling and transection of the tissue.

Figure 41:
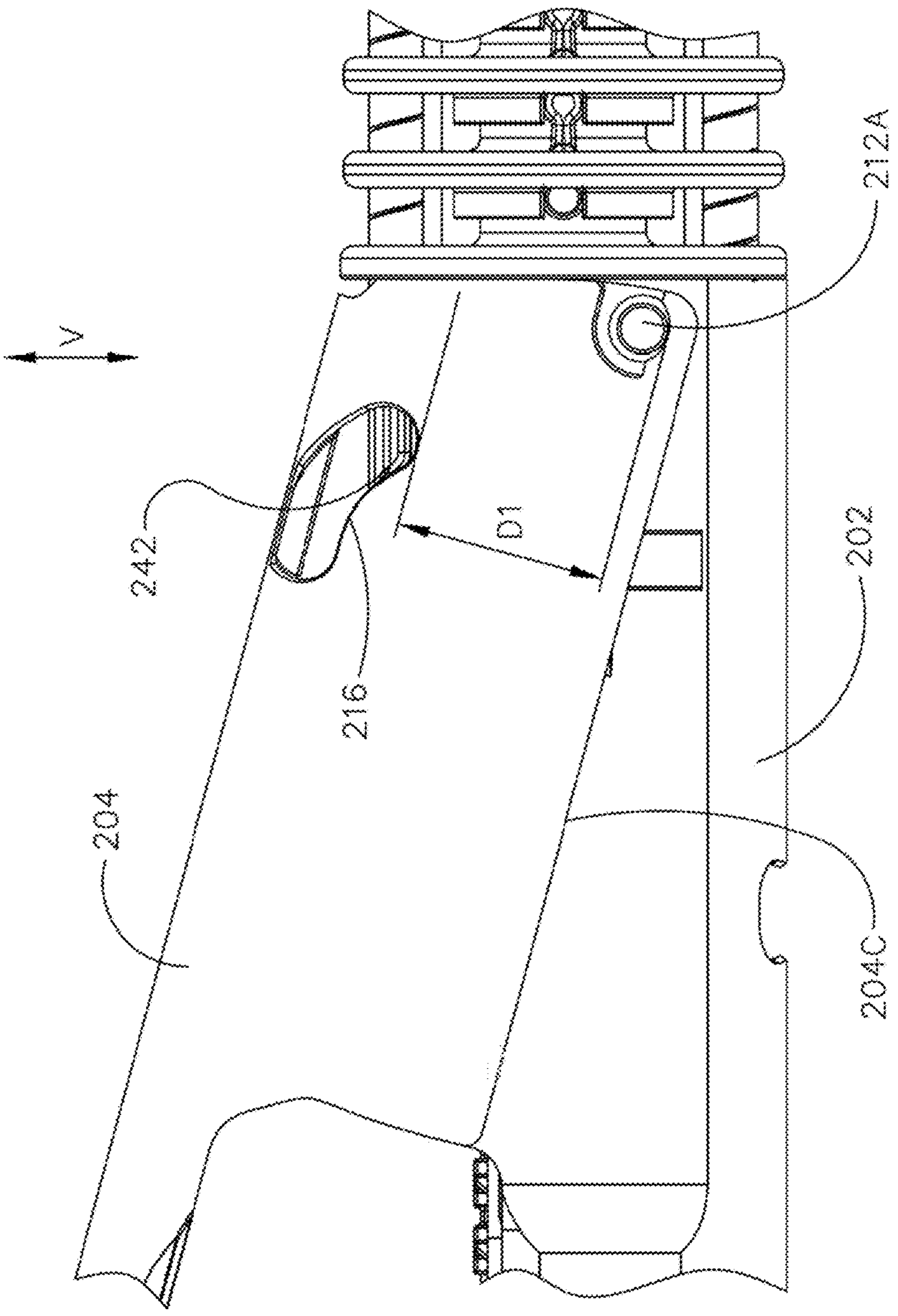
FIG. 41 is a schematic detail side view of an alternative proximal end configuration of the end effector, in accordance with the disclosed technology.

Making reference to FIG. 41, in alternative examples of the end effector 200, the pivot pin location can be positioned at a bottom, proximal corner of the anvil 204 (along a bottommost edge 204C thereof, e.g., within approximately 0.8-1 millimeters (e.g., 0.9 millimeters) of the bottommost edge 204C) such that the pivot pin 212A is disposed in a lower half of the end effector 200, relative to a vertical direction/axis V of the end effector 200. More specifically, the pivot pin 212A is spaced a predetermined distance D1 below a lowermost point of the ramp surface 216. This spacing maximizes the mechanical advantage of the anvil 204 (within the space constraints allowed by the components of the surgical instrument 1000) as the lateral wings 242 ride on the ramp surface 216 to cause rotation of the anvil 204 about the pivot point 212A. Thus, the force required to be applied to the driven knife 206 can be reduced. Moreover, increasing the mechanical advantage also allows the axial length of the ramp surface 216 to be shortened, thereby reducing the distance between the anvil 204/jaw 202 and the pivot location of the articulation joint 300. While shortening the ramp with respect to the pivot 212A reduces the mechanical advantage, by moving the pivot vertically downwards (in the V direction) as much as allowed by the surgical instrument's design, a similar knife load can be achieved with a shorter joint.

II. 2. End Effector and Hard Stop that Includes a Cleanout Port

Figure 39:
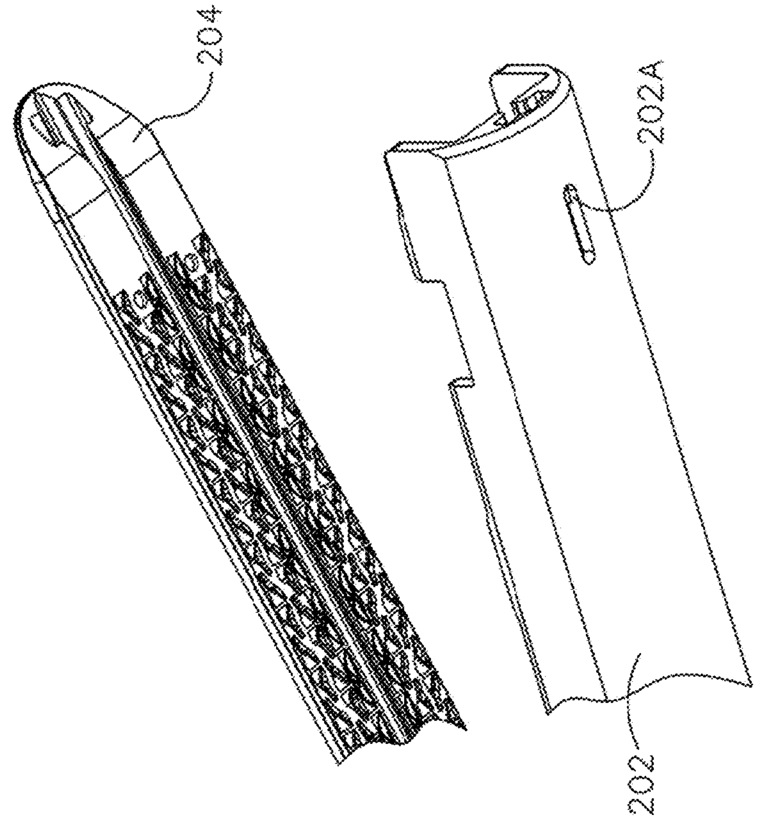
FIG. 39 is a schematic bottom detail view of the alternative distal end configuration of the end effector of FIG. 38, in accordance with the disclosed technology.
Figure 38:
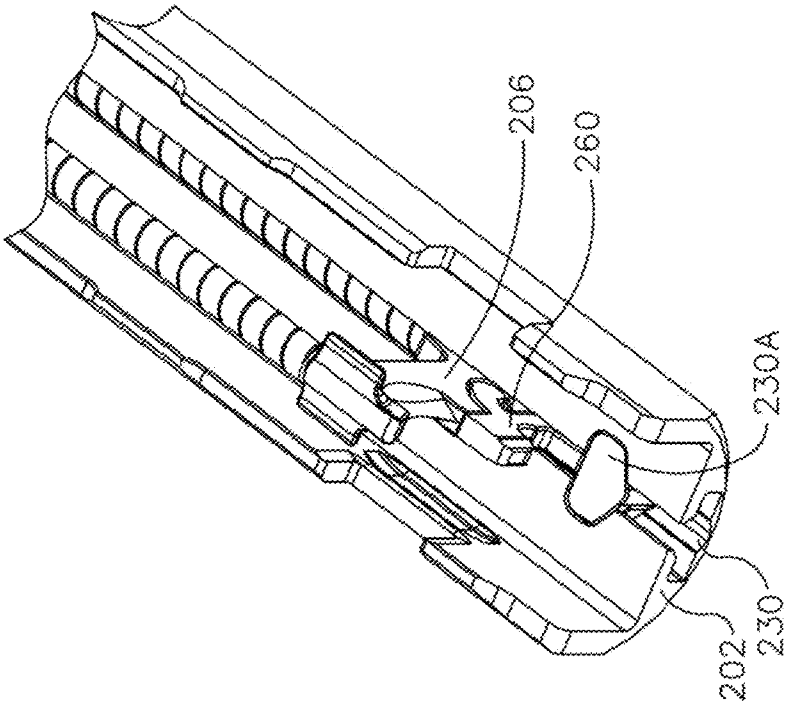
FIG. 38 is a schematic top detail view of an alternative distal end configuration of the end effector, with the anvil and cartridge of the end effector removed, in accordance with the disclosed technology.
Figure 40:
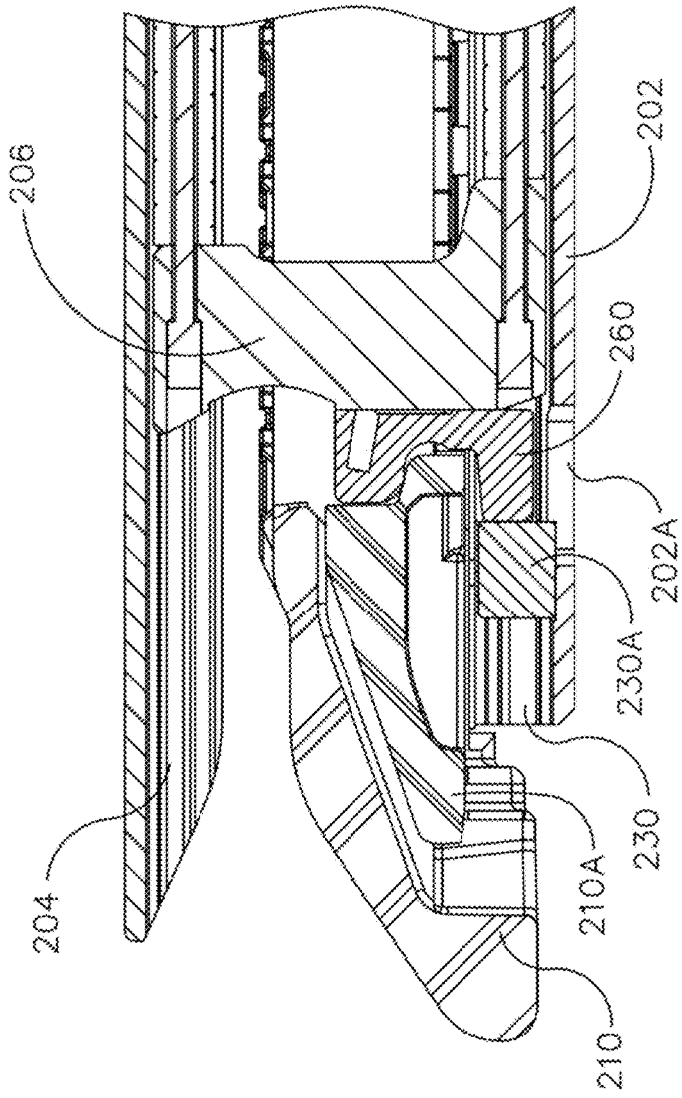
FIG. 40 is a schematic cross-sectional detail view of the alternative distal end of the end effector of FIG. 38, cut along a roll axis of the end effector, in accordance with the disclosed technology.

Reference is now made to FIGS. 38-40. In some embodiments, the jaw 202 further includes a mechanical hard stop 230A provided at the end of the cut path/line in the lower knife channel 230 (i.e., near a distal end thereof), which prevents the knife 206 from extending past the staple line and serves as an indicator to a robotic platform 2000 (discussed in greater detail below) that the knife 206 can be retracted. Moreover, a cleanout port 202A is formed (e.g., by milling which results in a semi-circular ends of the port 202A) through the jaw 202 into the lower knife channel 230 (in a transverse direction relative to the longitudinally extending channel 230) near the stop 230A. The cleanout port 202A serves as a passageway for fluid and debris to be discharged from the lower knife channel 230 that may otherwise accumulate while the knife 206 travels from the proximal end of the end effector 200 to the distal end thereof. In other words, the cleanout port 202A extends through a bottommost surface of the jaw 202 into the knife channel 230 so as to fluidically connect with the lower knife channel. In some embodiments, the cleanout port 202A partially overlaps with the stop 230A along the travel direction of the knife 206. This enhances the effectiveness of the cleanout port 202A because there are fewer surfaces adjacent the stop 230A for debris to becomes trapped and/or stuck to.

Figure 8D:
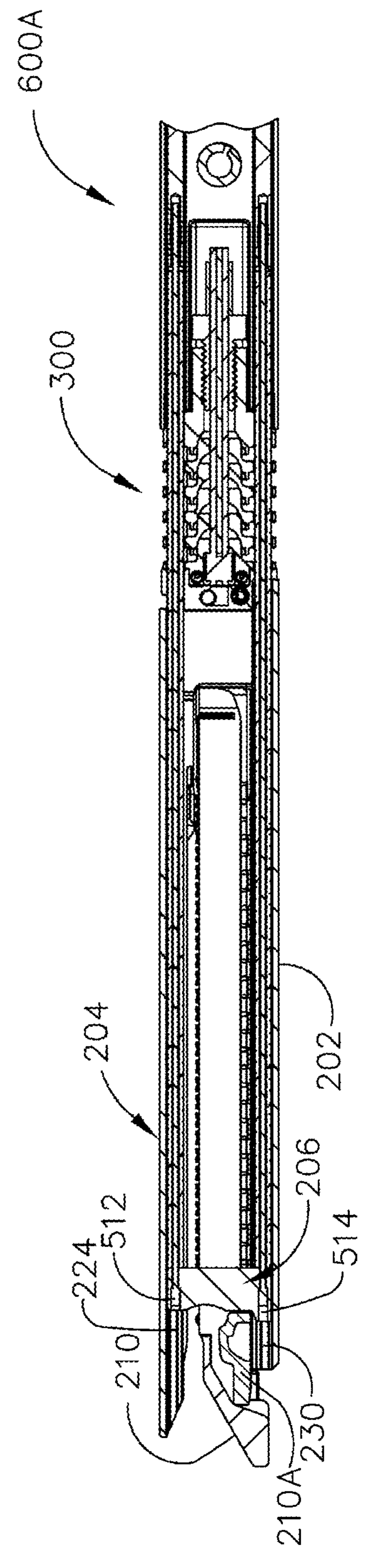
FIG. 8D is a schematic side cross-sectional view of the distal end of the surgical instrument, depicting the anvil in the clamping position with the knife fully advanced, in accordance with the disclosed technology.
Figure 9B:
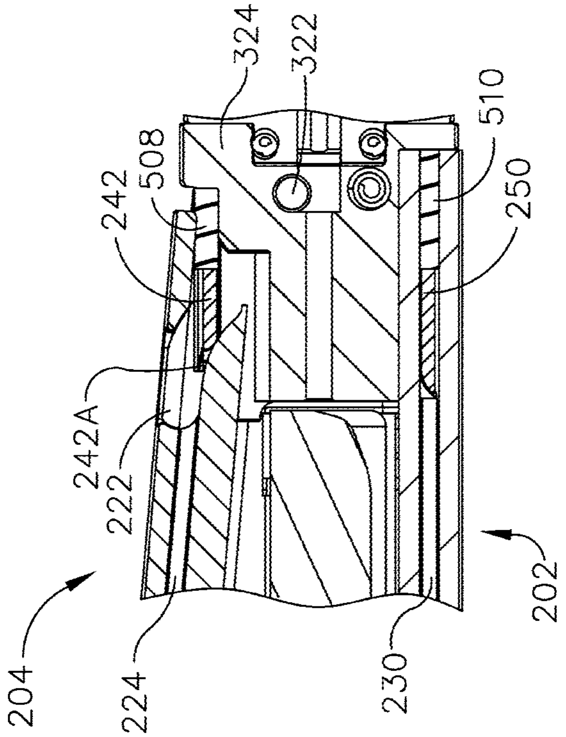
FIG. 9B is a schematic side cross-sectional detail view of the distal end of the surgical instrument, depicting the anvil in a grasping position with the knife partially advanced, in accordance with the disclosed technology.
Figure 9A:
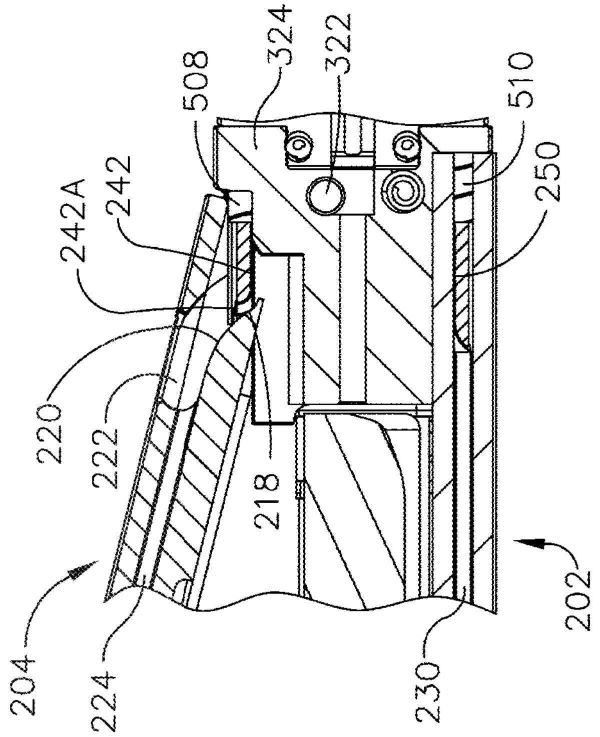
FIG. 9A is a schematic side cross-sectional detail view of the distal end of the surgical instrument, depicting the anvil in the open position, in accordance with the disclosed technology.
Figure 9D:
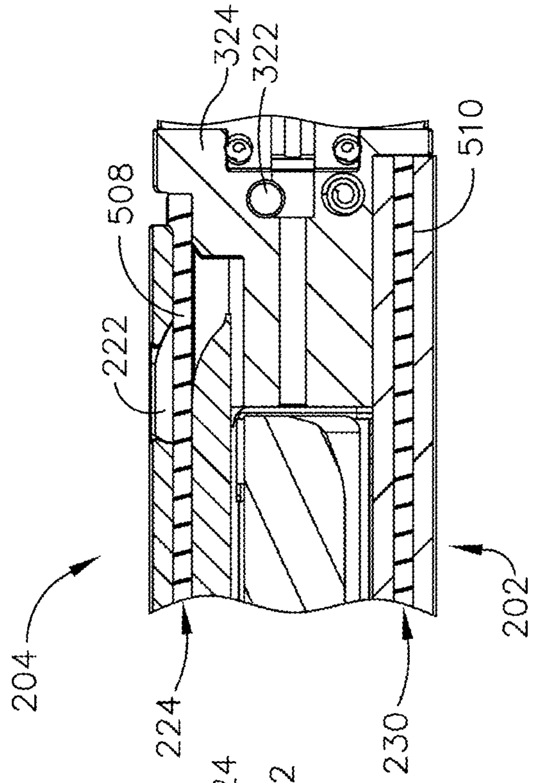
FIG. 9D is a schematic side cross-sectional view of the distal end of the surgical instrument, depicting the anvil in the clamping position with the knife fully advanced, in accordance with the disclosed technology.
Figure 9C:
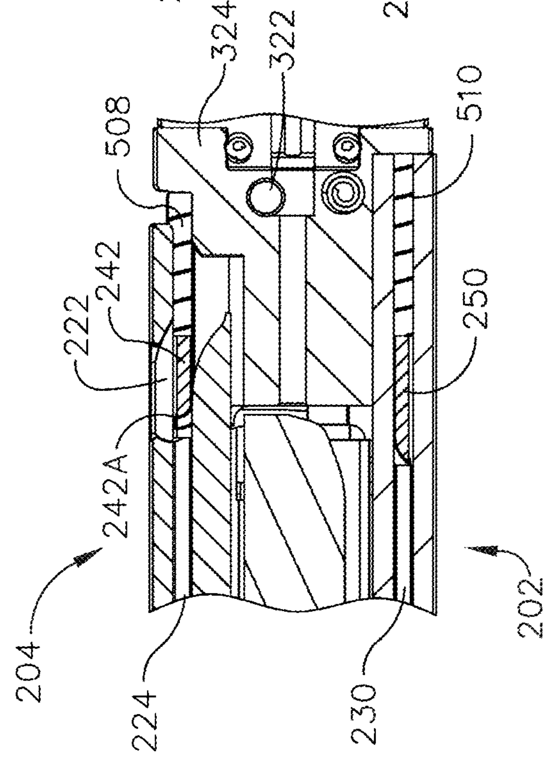
FIG. 9C is a schematic side cross-sectional detail view of the distal end of the surgical instrument, depicting the anvil in a clamping position with the knife partially advanced, in accordance with the disclosed technology.

As seen particularly in FIG. 40 (which shows the presently described example's knife 206 in a similar position as shown in FIG. 8D discussed above), a lockout mechanism 260 of the knife 206, which rides in the lower knife channel 230 as the knife 206 is fired, comes into contact with the stop 230A once the knife 206 has reached the end of the staple line. In this position, any debris that was present in the lower knife channel 230 and has been carried to along with the lockout mechanism 260 is either discharged through the cleanout port 202A or can by flushed out by an operator.

III. Overview of the Housing and Shaft Assembly

The surgical instrument 1000 further comprises a housing 700 and a shaft assembly 600A extending from the housing 700. The housing is configured to engage a robotic platform 2000. In some embodiments, the housing 700 may be configured as a handle (e.g., it may comprise a grip for a clinician). The shaft assembly 600A comprises a rotatable outer shaft 602 and an inner shaft 604, the outer shaft 602 being rotatably mounted to the housing about a rotation joint 606 (which may include one or more bearings). The inner shaft 604 is rotationally fixed to the outer shaft 602 and is configured such that articulation cables 402, 404, 406, 408, discussed in greater detail below, can be partially wound therearound without becoming tangled. As discussed in greater detail below, the housing 700 further comprises (1) a firing puck assembly 712 as part of the knife firing subsystem 500 operable to close the end effector 200, fire staples, and transect tissue, (2) a set of articulation puck assemblies 702, 704, 706, 708 as part of the articulation subsystem 400 operable to articulate the end effector 200 relative to the shaft assembly 600A, and (3) a shaft roll puck assembly 710 as part of the roll subsystem 600 configured to roll the outer shaft 602.

IV. Overview of the Articulation Subsystem

IV. 1. Articulation Joint

Figure 10:
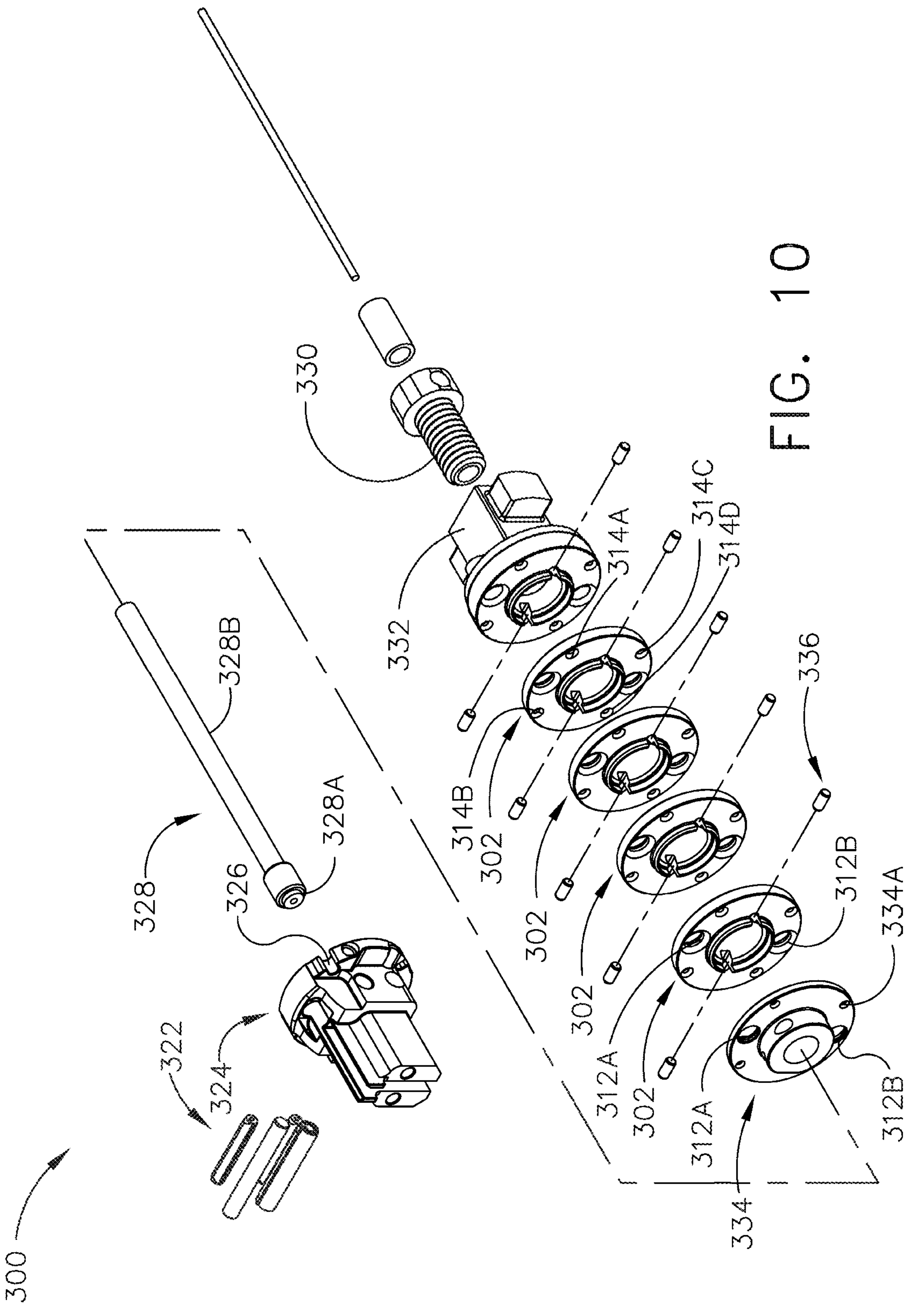
FIG. 10 is a schematic exploded view of the articulation joint, in accordance with the disclosed technology.
Figure 11:
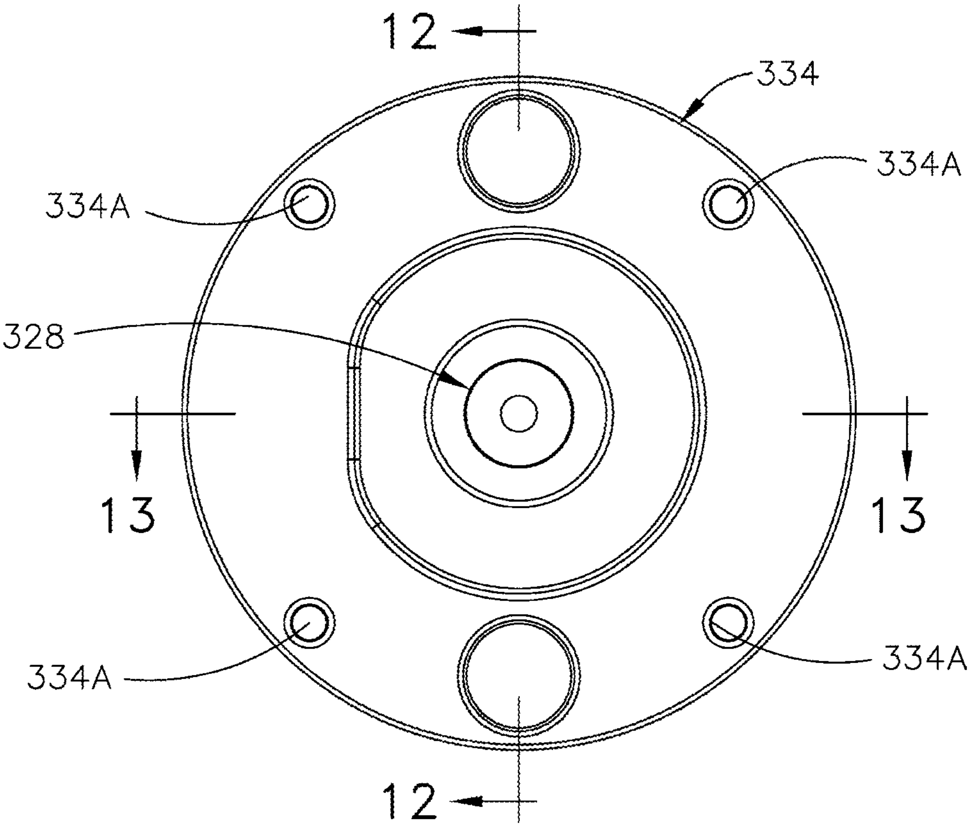
FIG. 11 is a schematic elevation view of the articulation joint, in accordance with the disclosed technology.
Figure 12:
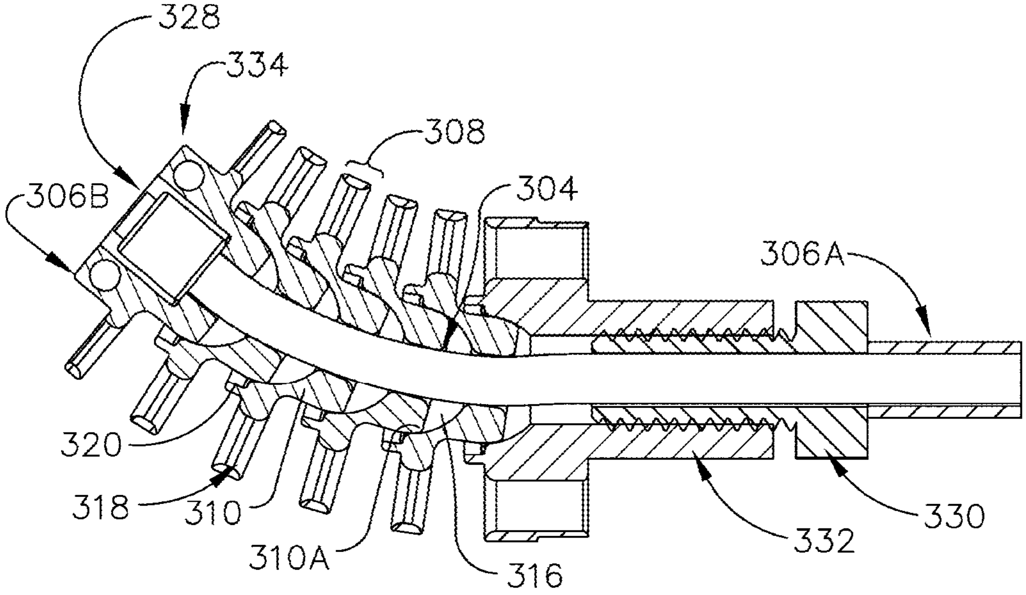
FIG. 12 is a schematic cross-sectional view of the articulation joint, cut relative to line 12-12 in FIG. 11; in accordance with the disclosed technology.
Figure 13:
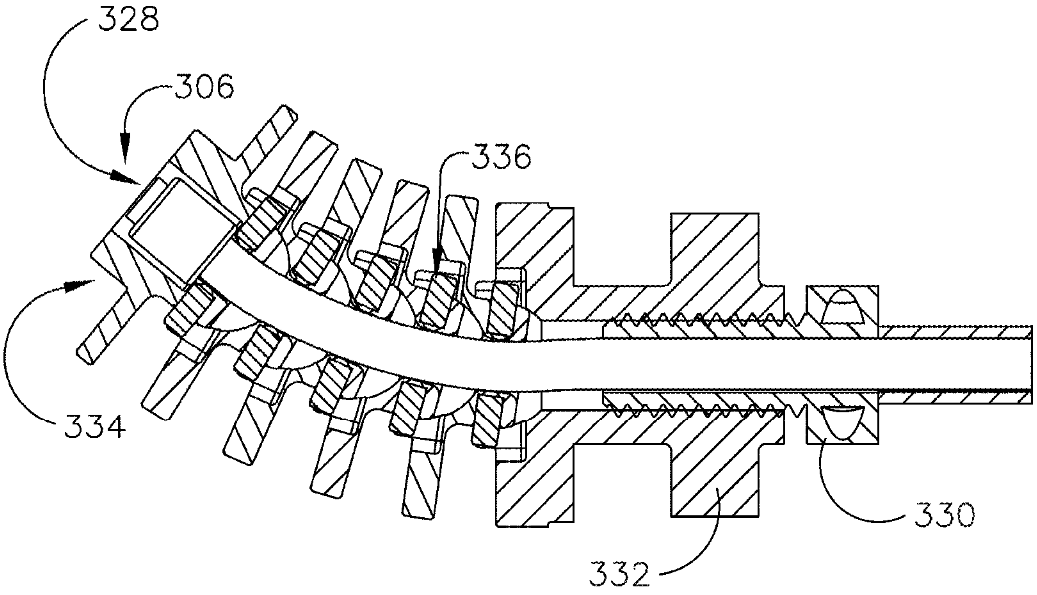
FIG. 13 is a schematic cross-sectional view of the articulation joint, cut relative to line 13-13 in FIG. 11; in accordance with the disclosed technology.
Figure 14:
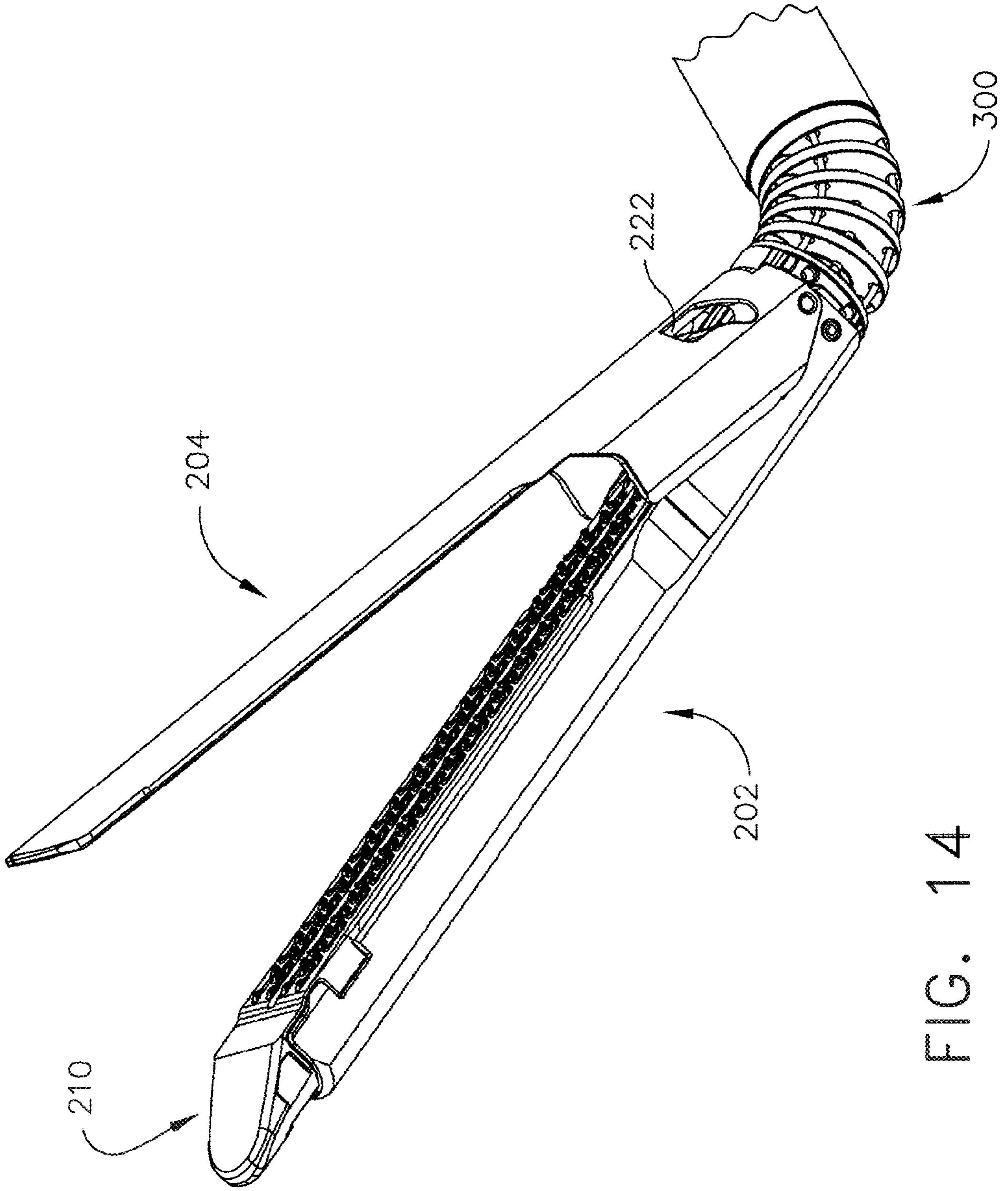
FIG. 14 is a schematic perspective detail view of the distal end of the surgical instrument, depicting the end effector pivoted vertically and laterally with the anvil open, in accordance with the disclosed technology.
Figure 15:
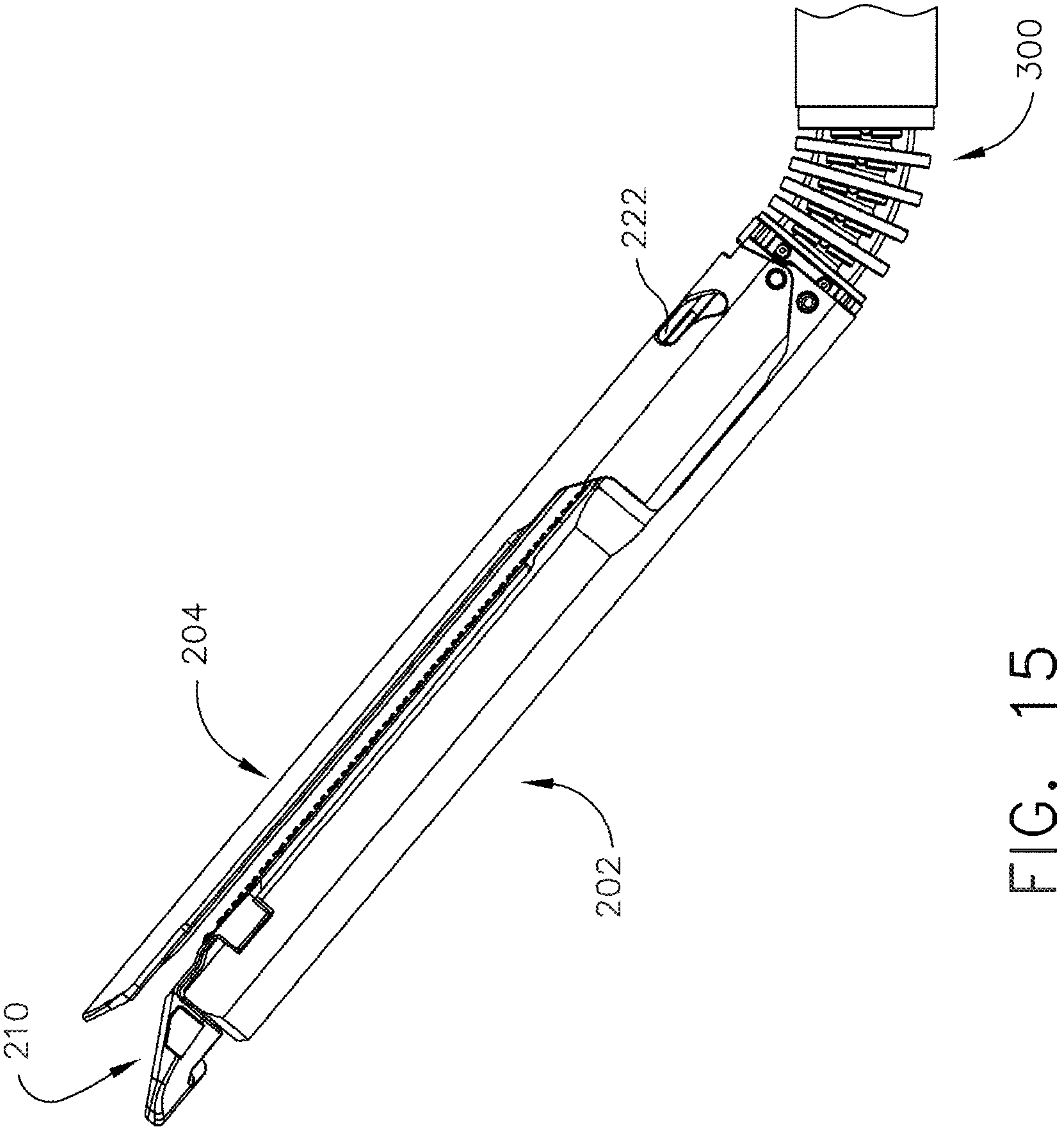
FIG. 15 is a schematic side detail view of the distal end of the surgical instrument, depicting the end effector pivoted vertically with the anvil closed, in accordance with the disclosed technology.
Figure 16:
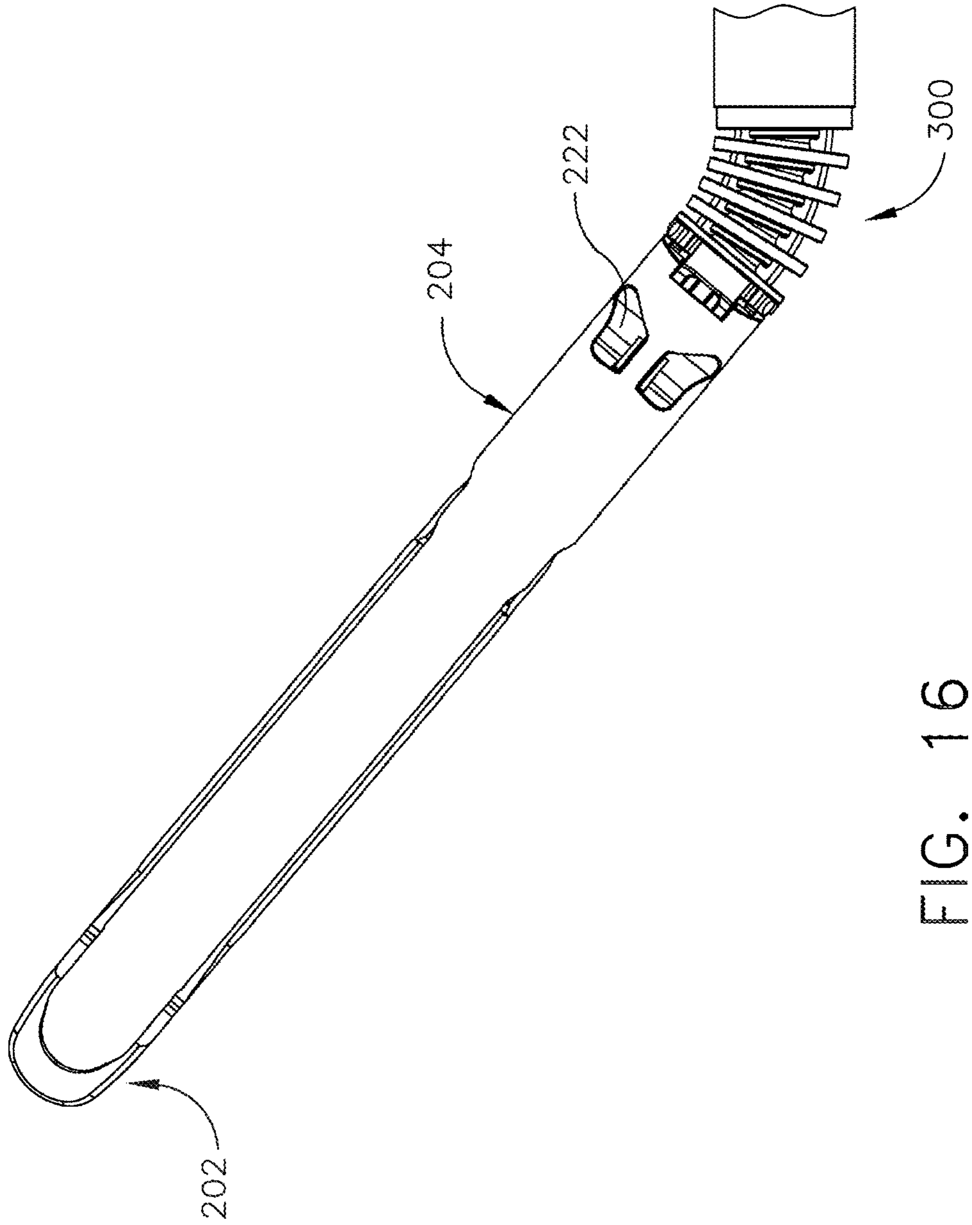
FIG. 16 is a schematic top detail view of the distal end of the surgical instrument, depicting the end effector pivoted laterally with the anvil closed, in accordance with the disclosed technology.

Referring to FIG. 10, the articulation joint 300 comprises a plurality of concentric discs 302 and a center beam assembly 306. Each concentric disc further includes a concentric central opening 304. The center beam assembly 306 has a proximal end 306A and a distal end 306B. As shown in FIGS. 12 and 13, a portion of the center beam assembly 306 extends through the central opening 304 of each concentric disc 302, and the center beam assembly 306 applies a compressive force to the concentric discs 302. The concentric discs 302 are nestably stacked on the center beam assembly 306 such that adjacent concentric discs 302 interface with one another. As seen in FIG. 7, the distal end 306B of the center beam assembly 306 couples to the plurality of concentric discs 302 to a proximal end of the end effector 200 of the surgical instrument 1000 (via one or more fasteners 322). As seen in FIG. 10, the distal end 306B includes a distal end retention disc 334 that defines a plurality of cable retention openings 334A. Further, the proximal end 306A of the center beam assembly 306 includes a second disc retention bearing 332 that is nested within and/or coupled with the shaft assembly 600A so as to couple the concentric discs 302 to the shaft assembly 600A. In some embodiments, the distal end 306B of the center beam assembly 306 abuts the knife sled 236.

As shown particularly in FIGS. 10, 12, and 13, each concentric disc 302 includes an articulation socket 308, an articulation pin 310 protruding outwardly from the articulation socket 308, a first push coil opening 312A defined through the articulation socket 308 and configured to receive a first push coil 508 therethrough, a second push coil opening 312B defined through the articulation socket 308 and configured to receive a second push coil 510 therethrough, and a plurality of articulation cable openings 314A-314D (e.g., a first articulation cable opening 314A, a second articulation cable opening 314B, a third articulation cable opening 314C, and a fourth articulation cable opening 314D) defined through the articulation socket 308 and configured to receive a respective articulation cable 402, 404, 406, 408 (e.g., a first articulation cable 402, a second articulation cable 404, a third articulation cable 406, and a fourth articulation cable 408) therethrough, and discussed in greater detail below. As shown in FIGS. 12 and 13, the concentric disc opening 304 is defined in the articulation pin 310 of each concentric disc 302. In some embodiments, three articulation cable openings 314A, 314B, 314C are provided to correspond to three articulation cables 402, 404, 406, while in other embodiments, four articulation cable openings 314A, 314B, 314C, 314D are provided to correspond to four articulation cables 402, 404, 406, 408.

Each concentric disc 302 further includes a rounded articulation pin proximal end 310A and a semi-spherical pin-receiving opening 316 defined in the articulation socket 308. As shown particularly in FIGS. 12 and 13, each rounded articulation pin proximal end 310A pivotally engages in an adjacent pin-receiving opening 316 of an adjacent concentric disc 302, with the exception of a proximal-most end 310A that engages with a second disc retention bearing 332. The articulation pin proximal end 310A and pin-receiving opening 316 interface functions in a similar manner as a swivel bearing. Moreover, the articulation socket 308 includes a socket disc 318 and a pin retention socket 320. A pair of pins 336 are used to provide rotational coupling about a primary axis of the shaft assembly 600A from one disc 302 to the next. In other words, the pins constrain a rotational degree of freedom between adjacent concentric discs 302) about the roll axis RA of the instrument 1000. In alternative embodiments, this feature can be integral to the disc 302 as opposed to the separate pins 336 shown in, e.g., FIG. 10.

Making particular reference to FIG. 10, the distal end 306B of the center beam assembly 306 includes a first disc retention bearing 324 that defines a plurality of clearance pockets 326. The center beam assembly 306 also further includes a center beam 328 extending through each of the concentric discs 302, a jack screw 330, and a second disc retention bearing 332. The jack screw 330 is threadably coupled with the second disc retention bearing 332 to adjust a compressive force of the center beam 328 (i.e., it can be used to adjust pre-tension of the articulation joint 300). The center beam assembly 326 keeps the discs 302 together and also reacts the firing load so that it does not react on the articulation cables (which are discussed in greater detail below).

The center beam 328 further includes a nitinol core 328A and stainless steel 328B wound over the nitinol core that allows the center beam 328 to resiliently flex in response to pivoting of one, some, or all of the concentric discs 302. The wound stainless steel 328B has clockwise braiding and counterclockwise braiding to prevent unwinding thereof.

The above-described articulation joint 300 forms a portion of the cable articulation subsystem 400 which allows for precise 360-degree movement of the end effector 200 about the articulation joint 300 with at least two degrees of freedom. In some embodiments, and dictated by the roll subsystem 600 as well as a need to limit the amount of wrap of the articulation cables 402, 404, 406, 408, the articulation joint is permitted about 320 degrees of roll within the overall system. The cable articulation subsystem 400 also includes a plurality of articulation cables 402, 404, 406, 408 each having a distal end 402A, 404A, 406A, 408A, coupled to the distal end 306B of the center beam assembly 306, and a proximal end 402B, 404B, 406B, 408B. More specifically, each distal end 402A, 404A, 406A, 408A can include a crimp that engages a cable retention opening 334A of the distal end retention disc 334 to maintain its positioning.

IV. 2. Articulation Cables

Each articulation cable 402, 404, 406, 408 includes a stainless steel material with clockwise braiding and counterclockwise braiding that prevent unwinding thereof. In other embodiments, other materials may be employed, such as polymer yarns and/or filaments, various metal cables (e.g., tungsten), and combinations thereof. Each articulation cable is discretely manipulable to cause rotation of the articulation joint 300 and end effector 200 about at least one of a pitch axis PA and a yaw axis YA.

In some embodiments, three articulation cables may be provided rather than the four cables 402, 404, 406, 408 depicted herein. However, four articulation cables 402, 404, 406, 408 circumferentially spaced approximately ninety degrees from one another (as shown) provides load splitting. Additionally, in alternative embodiments, three and fourth articulation cable configurations may be spaced non-symmetrically relative to one another.

Figure 35:
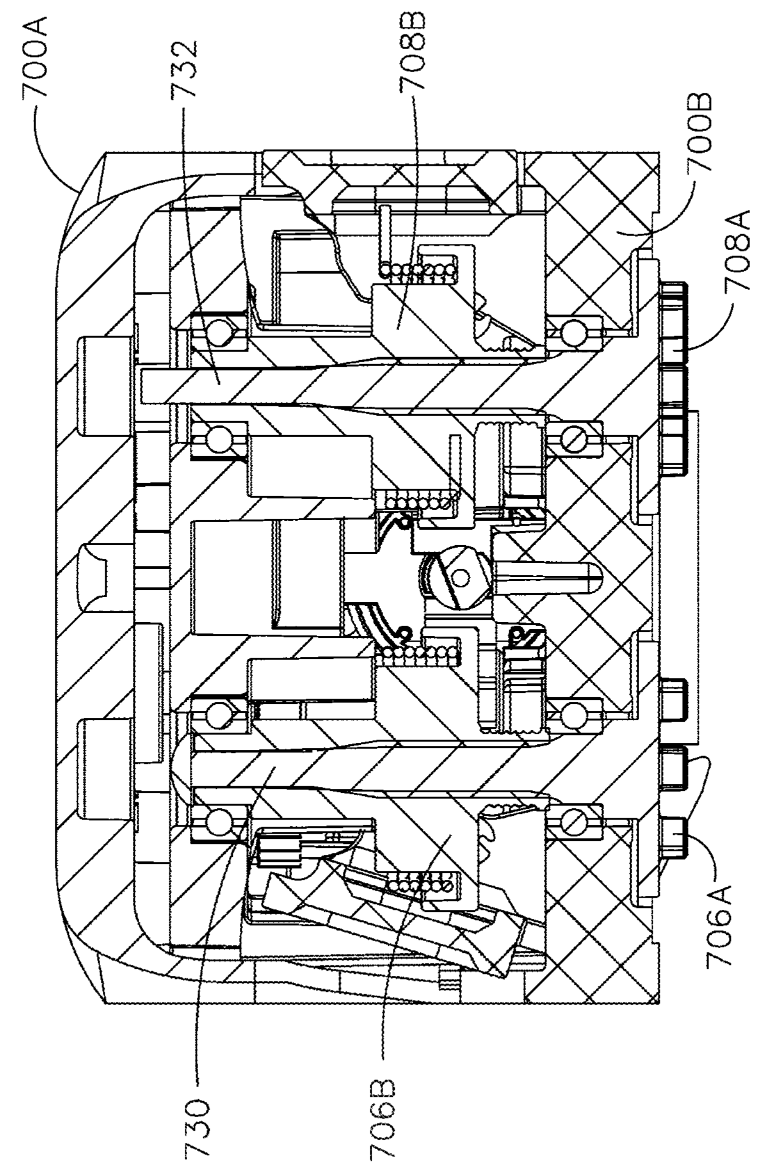
FIG. 35 is a schematic cross-sectional view of the housing, cut relative to line 35-35 in FIG. 32; in accordance with the disclosed technology.
Figure 36:
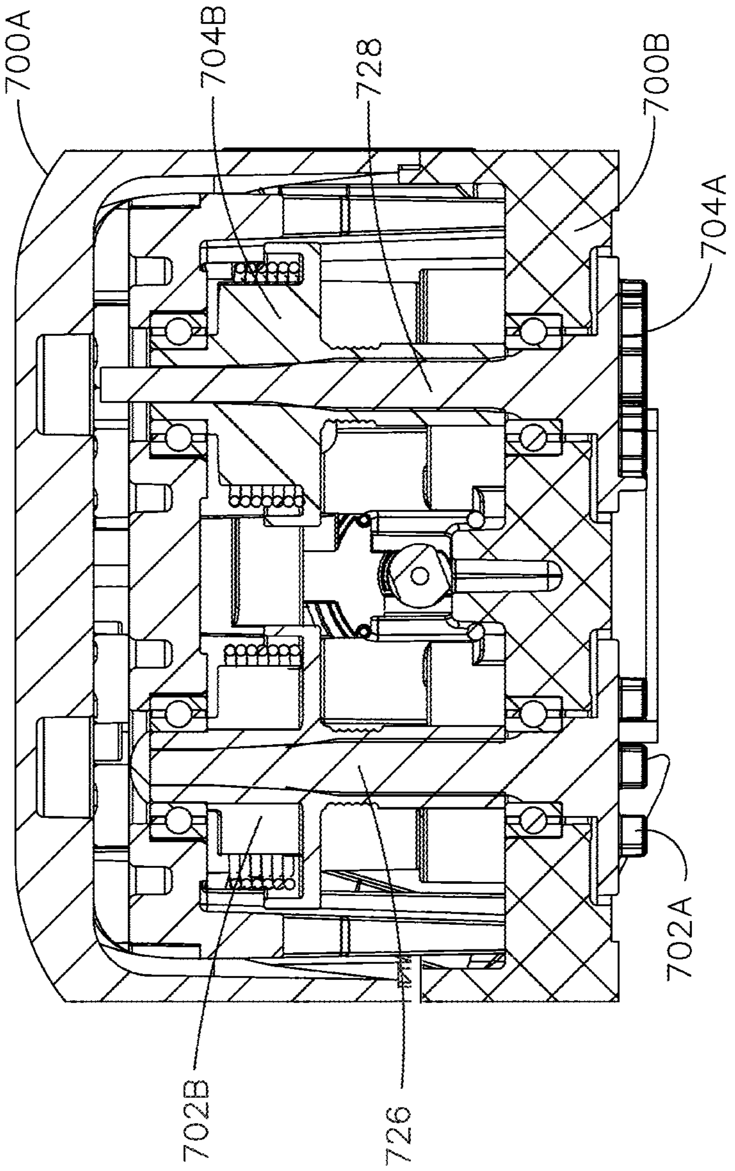
FIG. 36 is a schematic cross-sectional view of the housing, cut relative to line 36-36 in FIG. 32; in accordance with the disclosed technology.

The shaft assembly 600A and housing 700 also form portions of the cable articulation subsystem 400. More specifically, each articulation cable 402, 404, 406, 408 extends from the articulation joint 300 and through the shaft assembly 600A to the housing 700. The proximal end 402B, 404B, 406B, 408B of each articulation cable (402, 404, 406) is movably mounted in the housing 700 which causes the above-mentioned rotation of the articulation joint 300 and end effector 200. In some embodiments, the housing 700 includes articulation puck assemblies 702, 704, 706, 708 with rotatable capstans 702B, 704B, 706B, 708B, discussed in greater detail below, about which corresponding proximal ends 402B, 404B, 406B, 408B of the articulation cables 402, 404, 406, 408 are windably mounted thereto. As shown in FIGS. 35 and 36, the capstans 702B, 704B, 706B, 708B can be vertically offset from one another (e.g., capstan 702B and capstan 704B can be located proximal one portion 700A of the housing 700, and capstan 706B and capstan 708B can be located proximal another portion 700B of the housing 700.

The articulation cables 402, 404, 406, 408 are routed through the shaft assembly 600A such that they are disposed between the outer shaft 602 and the inner shaft 604, with the articulation cables 402, 404, 406, 408 being able to partially wind therearound without becoming tangled. The inner shaft 604 also prevents the articulation cables 402, 404, 406, 408 from interfering with other components running down the center of the instrument 1000 (through the inner shaft 604).

IV. 3. Articulation Joint and Articulation Cable Connection/Operation

The articulation cables 402, 404, 406, 408 are routed and coupled to the end effector 200 via the articulation joint 300 such that movement thereof in a proximal direction (via winding about the capstans 702B, 704B, 706B, 708B) causes the end effector 200 to pivot in a predetermined manner about the articulation joint 300. For example, actuation of the first articulation cable 402 in the proximal direction causes rotation of the end effector 200 upwards and to the left, actuation of the second articulation cable 404 in the proximal direction causes rotation of the end effector 200 upwards and to the right, actuation of the third articulation cable 406 in the proximal direction causes rotation of the end effector 200 downwards and to the left, and actuation of the fourth articulation cable 408 in the proximal direction causes rotation of the end effector 200 downwards and to the right. Similarly, movement of two articulation cables simultaneously will result in blended movement of the end effector 200. By way of example, movement of both the first articulation cable 402 and the second articulation cable 404 at the same rate causes only upwards pivoting of the end effector 200 (i.e., there is little to no horizontal component to the rotation). As will be appreciated by those skilled in the art, this configuration provides for the above-mentioned precise 360-degree movement of the end effector about the articulation joint 300 with at least two degrees of freedom and about 320 degrees of roll.

V. Overview of the Firing Subsystem

Referring primarily to FIGS. 2, 8A-8D, 9A-9D, 17 and 23, the knife firing subsystem 500 includes the aforementioned knife 206, the aforementioned sled 236, a firing rod 502 that drives the knife 206 and/or sled 236, a first push rod 504, and a second push rod 506. The firing rod 502 includes a firing rod rack 530 and is driven by a firing puck assembly 712, which is described in greater detail below. The first push rod 504 has a first push rod distal end 504A coupled to the sled 236 and a first push rod proximal end 504B coupled to the firing rod 502. Similarly, the second push rod has a second push rod distal end 506A coupled to the sled 236 and a second push rod proximal end 506B coupled to the firing rod 502. The distal ends 504A, 506A are coupled to respective upper and lower portions of the sled 236 (e.g., the upper knife tab 238 and the lower knife tab 246), which enables the knife 206 to be pushed evenly at its ends. In some embodiments, the proximal ends 504B, 506B of the push rods 504, 506 are coupled to the firing rod via a differential 520, which is discussed in greater detail below.

The knife firing subsystem 500 is configured in a manner to enable articulation of the end effector 200 while still enabling proper functionality of the knife 206. To that end, the first push rod 504 includes a first flexible section 508 and the second push rod 506 comprises a second flexible section 510. As particularly shown in FIGS. 20-22, the flexible sections 508, 510 rout through the articulation joint 300 via the respective push coil openings 312A, 312B and the push rods 504, 506 engage the respective tab openings 244, 252 in the sled 236. More specifically, the first flexible section 508 includes a first push coil 508 and a first center cable 512 extends through the first push coil 508 to engage the sled 236 via a barrel crimp, and the second flexible section 510 includes a second push coil 510 and a second center cable 514 extends through the second push coil 510 to engage the sled 236 via a barrel crimp. The push coils 508, 510 provide the rods 504, 506 sufficient stability to deliver a firing force to the knife 206, while not being too stiff that would prevent articulation at the joint 300. The cables 512, 514, which are engaged with the sled 236 as discussed above (see, e.g., FIG. 8A), prevent the coils 508, 510 from stretching and/or elongating and serve as retraction cables when the rods 504, 506 are retracted towards the proximal end of the surgical instrument 1000.

Figure 20:
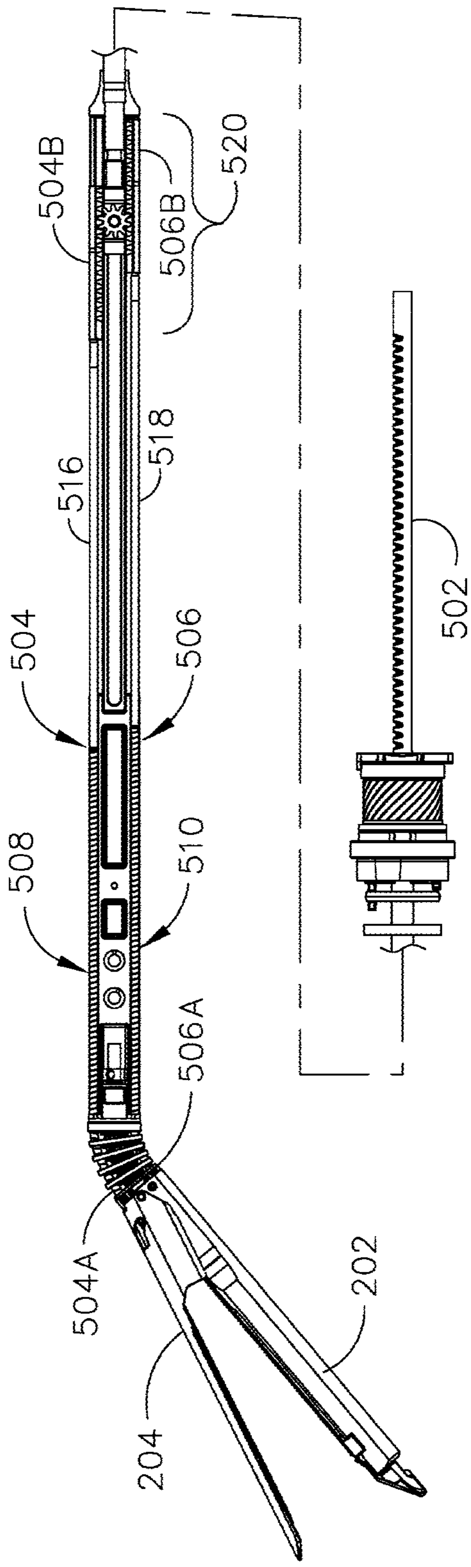
FIG. 20 is a schematic side view of the firing subsystem, depicting the end effector pivoted vertically downwards and the anvil in the open position, in accordance with the disclosed technology.
Figure 21:
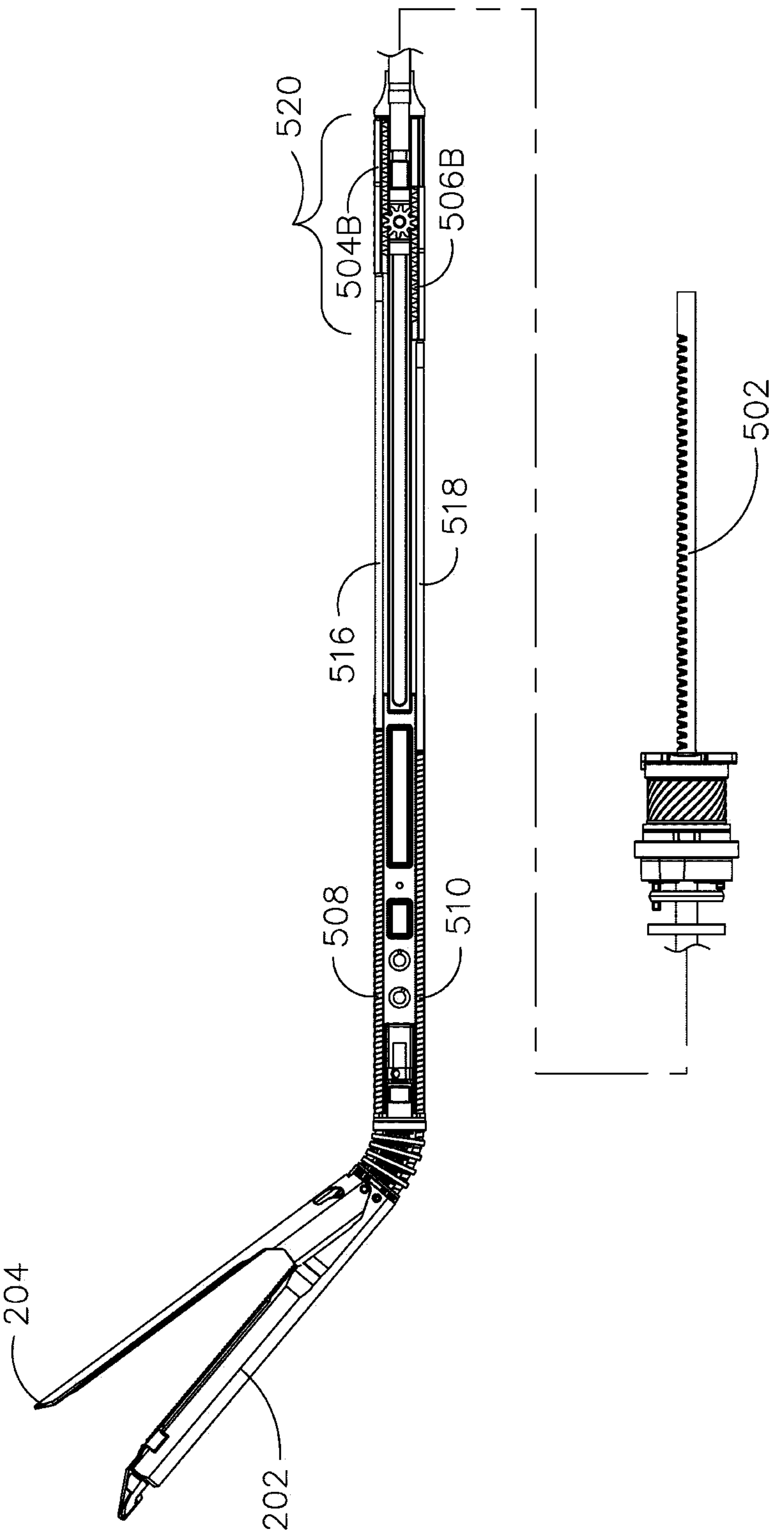
FIG. 21 is a schematic side view of the firing subsystem, depicting the end effector pivoted vertically upwards and the anvil in the open position, in accordance with the disclosed technology.
Figure 22:
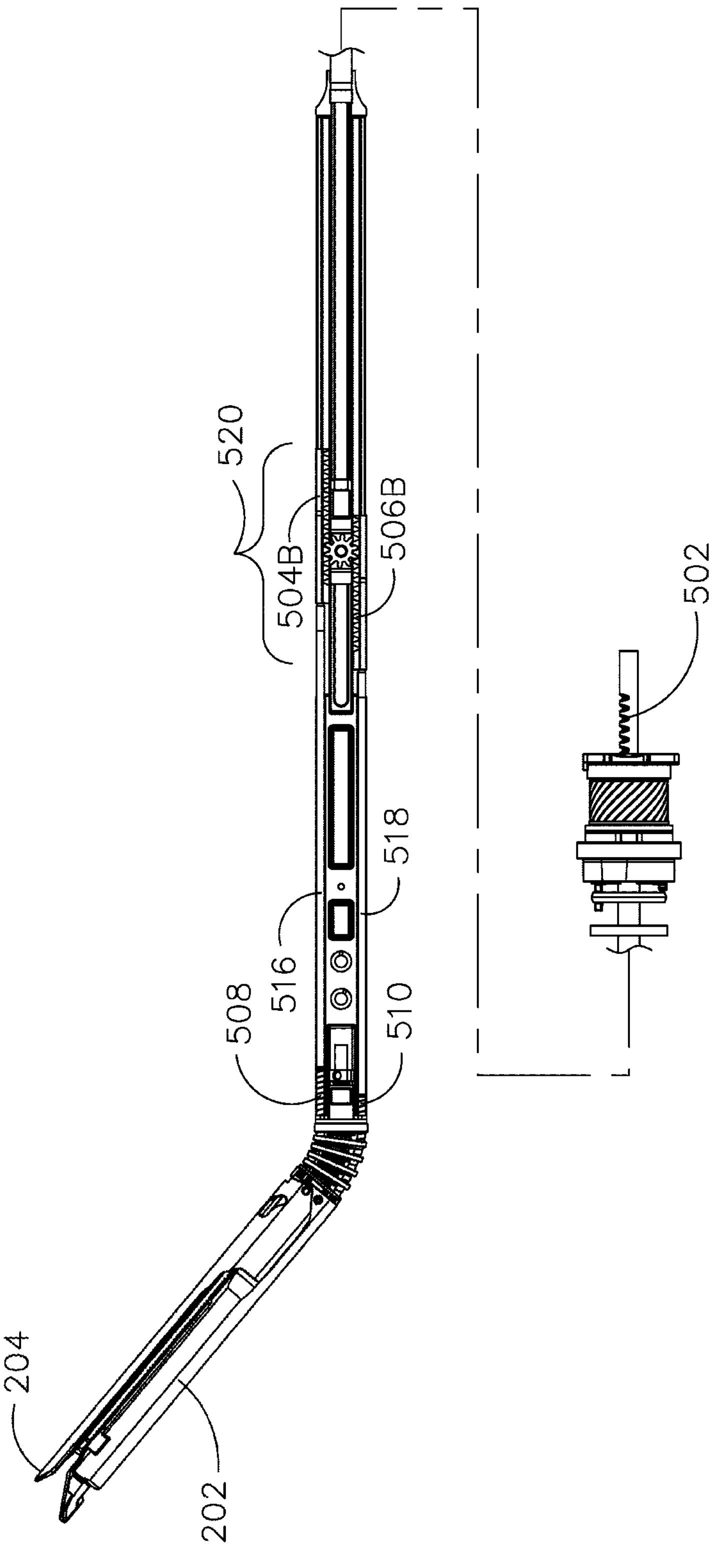
FIG. 22 is a schematic side view of the firing subsystem, depicting the end effector pivoted vertically upwards and the anvil in the clamping position and the knife fully advanced, in accordance with the disclosed technology.
Figure 23:
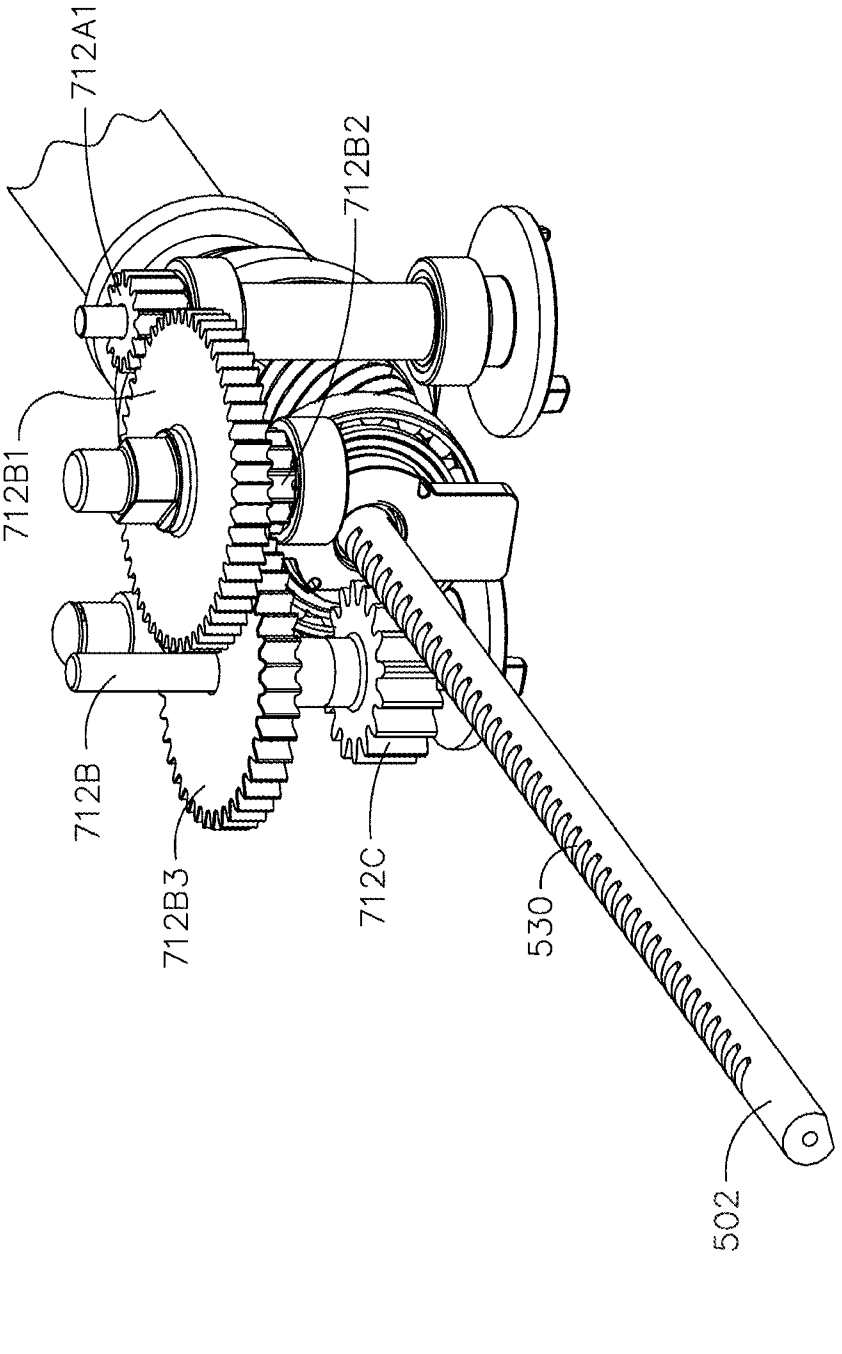
FIG. 23 is a schematic detail view of the proximal end of the surgical instrument, depicting portions of the knife firing subsystem, in accordance with the disclosed technology.

With continued reference to FIGS. 20-22, the entirety of the push rods 504, 506 do not bend and/or extend through the articulation joint 300, in use, and therefore does not need to be flexible. Accordingly, a proximal section of each push rod 504, 506 includes a rigid rod 516, 518. As used, the term 'rigid' refers to a structure less flexible than the described push coils 508, 510 and cables 512, 514. Specifically, the first push rod 504 includes a first rigid rod 516 coaxial with and coupled to the first push coil 508 and first center cable 512, and the second push rod 506 includes a second rigid rod 518 coaxial with and coupled to the second push coil 510 and second center cable 514.

Further to the above, depending on the manner in which the end effector 200 is pivoted about the articulation joint 300, the bend radius for the first push coil 508 and the second push coil 510 can differ. For example, in the configuration shown in FIG. 21 (i.e., when the end effector 200 is pivoted upwards), the first push coil 508 has a smaller bend radius than the second push coil 510, leading to a greater amount of the second push coil 510 extending through the articulation joint 300 than the first push coil 508. A differential 520 is provided to account for these differing bend radii, as well as to balance any difference in loading, ensuring an even split of the firing force being delivered to the push rods 504, 506.

More specifically, the differential 520 couples the first push rod proximal end 504B and the second push rod proximal end 506B to the firing rod 502, and the differential 520 permits relative axial movement between the first push rod 504 and the second push rod 506 (e.g., as depicted from FIG. 20 to FIG. 21). The differential 520 includes a first rack 522 coupled to the first push rod 504, a second rack 524 coupled to the second push rod 506, a pinion bar 526 coupled to the firing rod 502, and a pinion 528 rotatably mounted on the pinion bar 526 and meshed with the first rack 522 and the second rack 524.

Further to the above, as particularly exemplified in FIGS. 20-21, the first rack 522 and the second rack 524 are movable in opposing axial directions relative to one another in response to rotation of the sled 236 about the pitch axis PA to account for the aforementioned differing bend radii of the push coils 508, 510.

Further, as shown in FIG. 22, the first rack 522 and the second rack 524 are each movable in the same axial direction (e.g., a first axial direction) in response to movement of the firing rod 502 in the first axial direction with a firing force. As discussed above, this firing force is delivered through the push coils 508, 510 to the knife 206, which closes the anvil 204 to a grasping position and/or a clamping position. As shown in the sequence depicted in FIGS. 9A-9D, movement of the push coils 508, 510 distally results in them riding in the central upper knife channel portion 226 of the upper knife channel 224 and the central lower knife channel portion 232 of the lower knife channel 224, respectively. Further movement of the firing rod 502 in the first axial direction continues movement of the knife 206 to fire the staples and transect tissue, as discussed above. Retraction of the knife 206 and opening of the anvil is achieved by moving the firing rod 502 in an opposite, second direction. As demonstrated in FIGS. 21 and 22, due to the independent cable articulation system 400 and knife firing system 500, the knife 206 and sled 236 can be oriented and translate non-parallel to an orientation and movement of the firing rod 502.

In order to permit roll of the shaft outer shaft 602, which is discussed in greater detail below, the differential 520 is mounted in the shaft assembly 600A and is coupled to the firing rod 502 such that it is rotatable about a roll axis RA. As a result, the pinion bar 526 is axially constrained relative to the firing rod 502 and freely rotatable relative thereto.

VI. Overview of the Roll Subsystem

Figure 19:
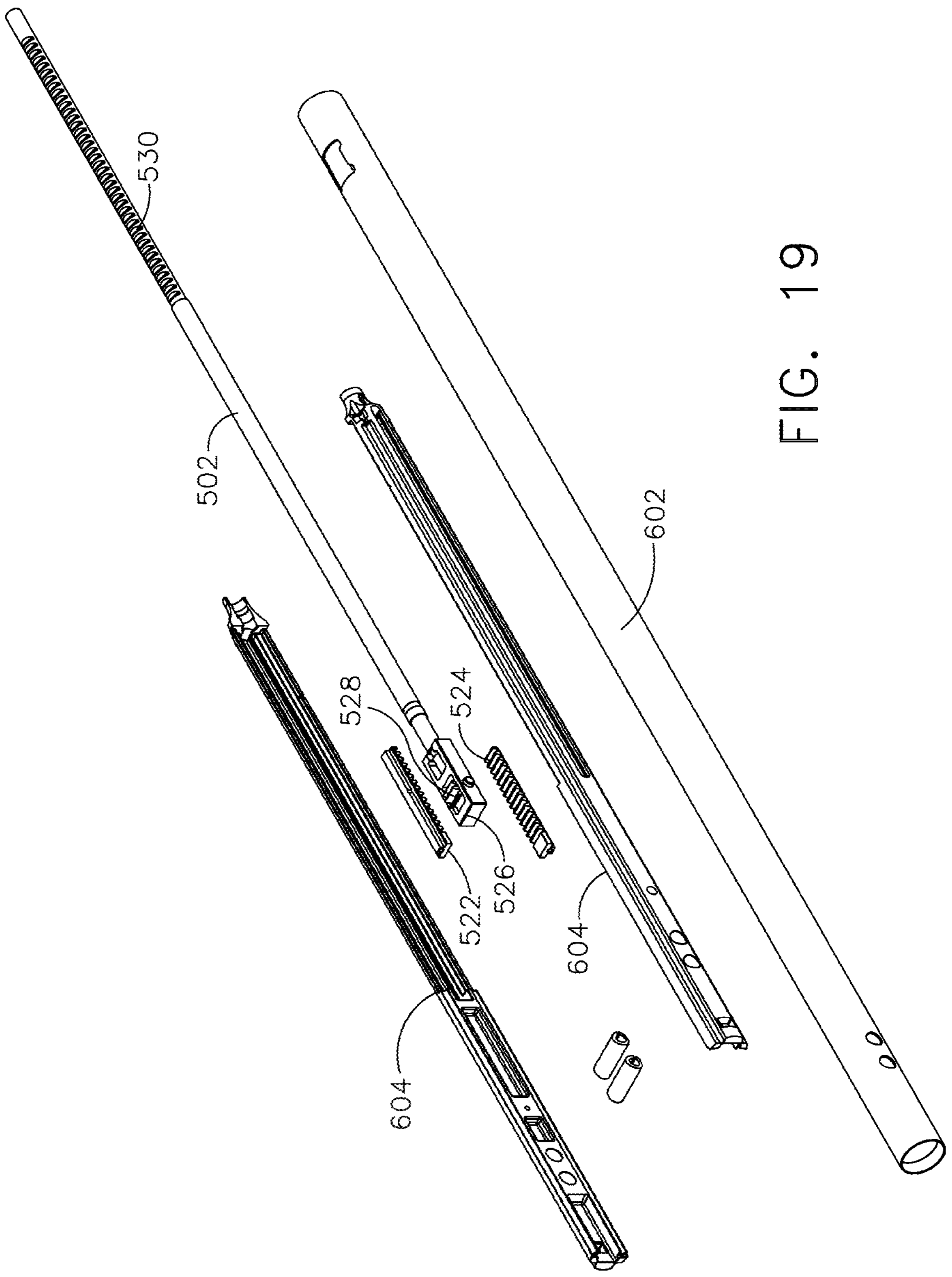
FIG. 19 is a schematic perspective view of a shaft assembly, a differential, and a firing rod of the surgical instrument, in accordance with the disclosed technology.
Figure 24:
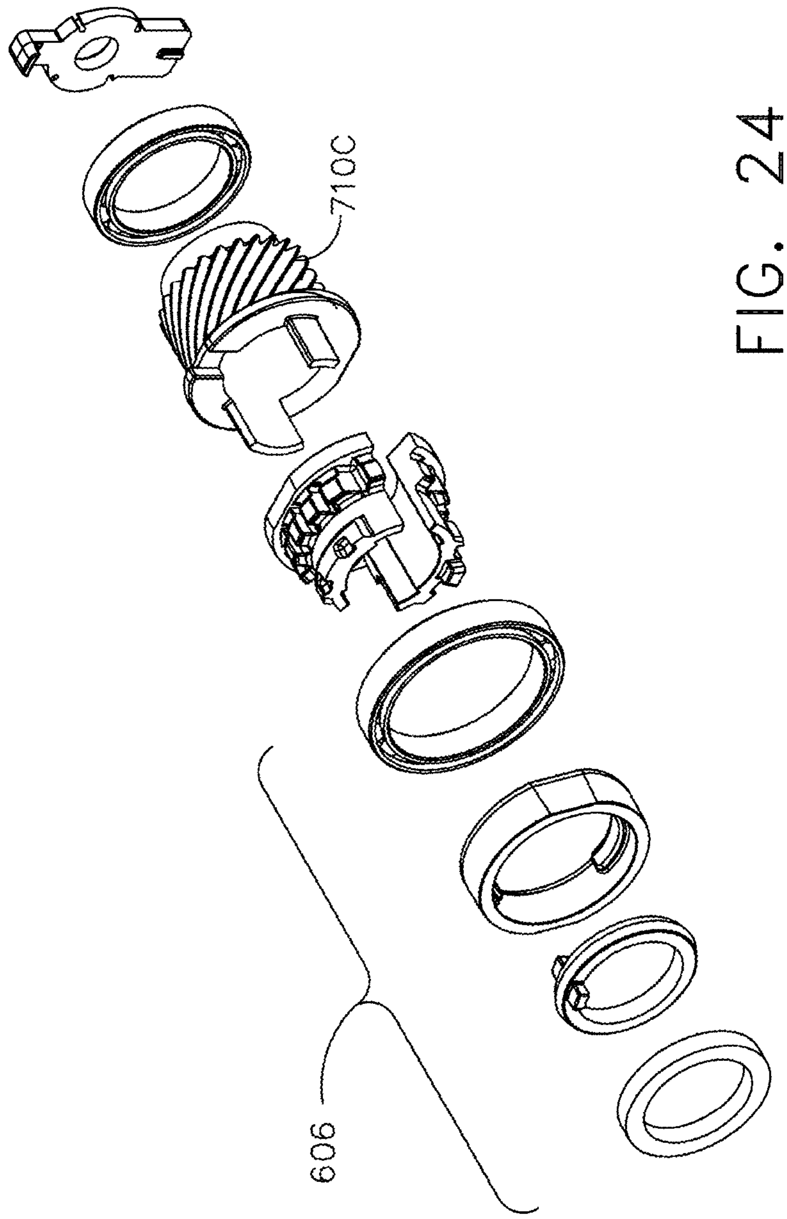
FIG. 24 is a schematic exploded detail view of a rotation joint, in accordance with the disclosed technology.
Figure 25:
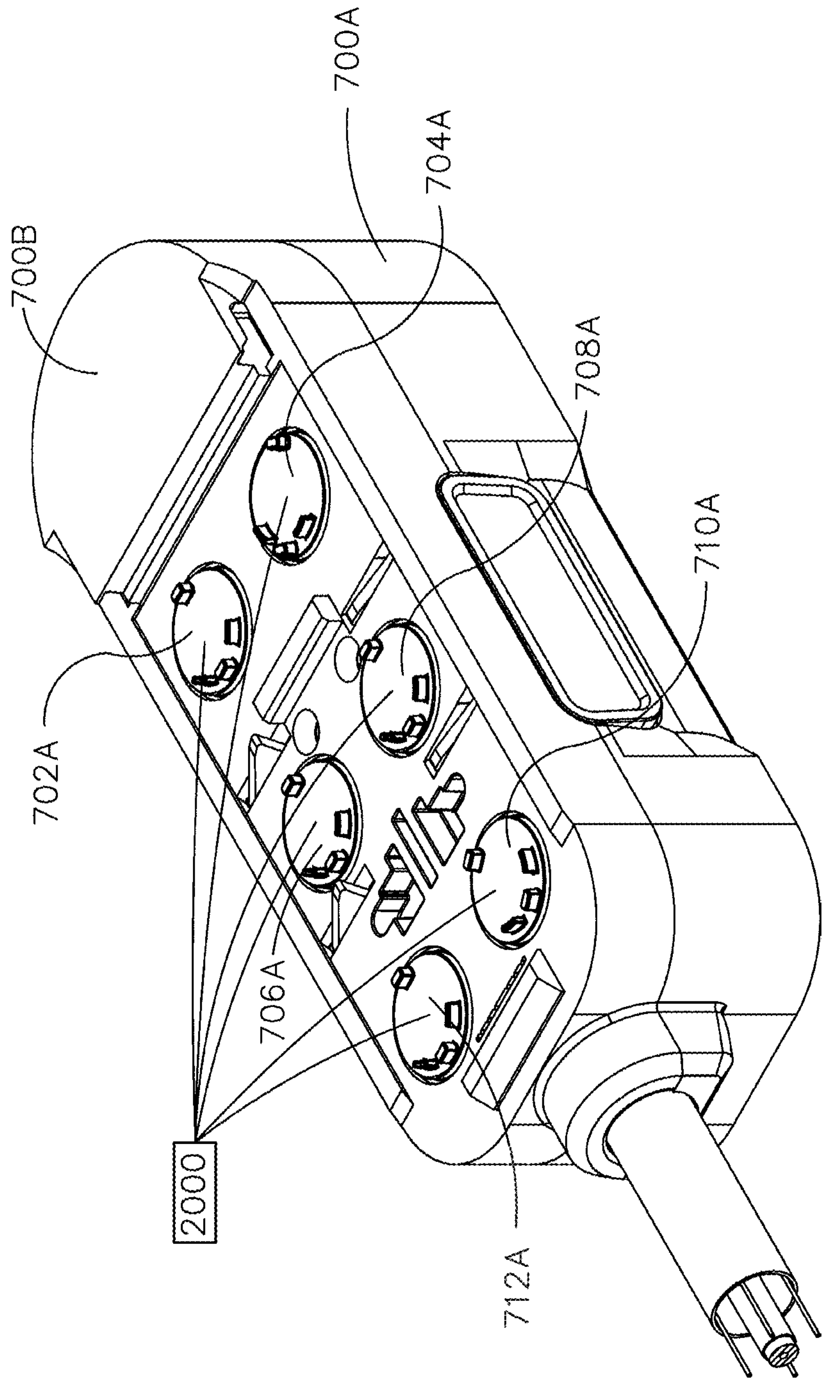
FIG. 25 is a schematic detail view of one side of a housing, depicting rotational pucks that engage a robotic platform, in accordance with the disclosed technology.
Figure 26:
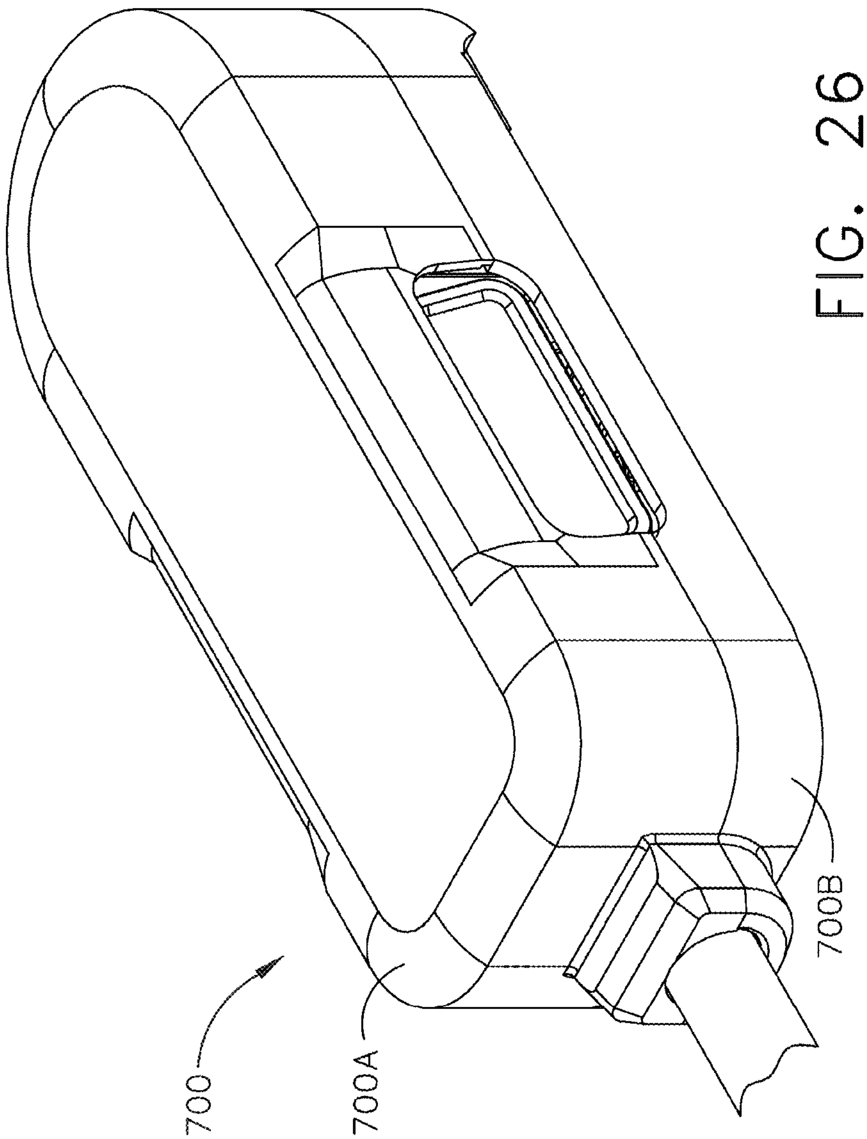
FIG. 26 is a schematic detail view of another side of the housing, in accordance with the disclosed technology.
Figure 27:
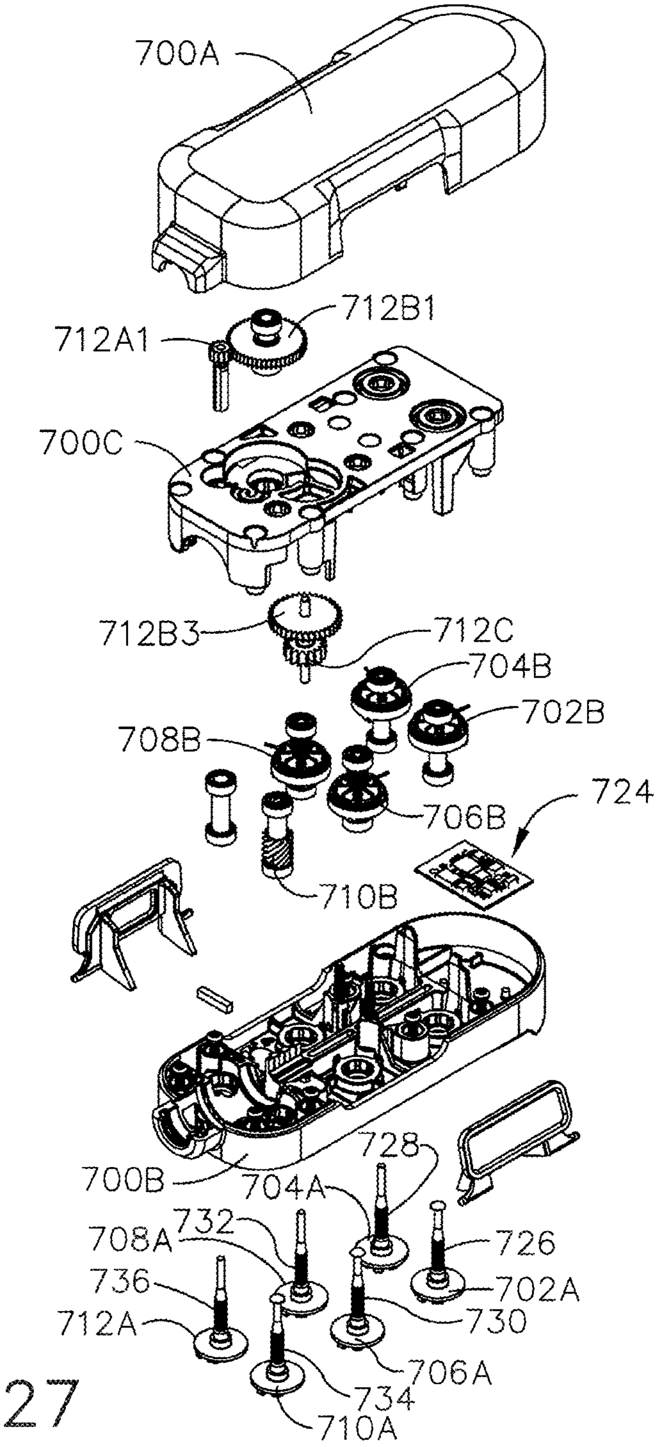
FIG. 27 is a schematic exploded view of the housing, in accordance with the disclosed technology.
Figure 28:
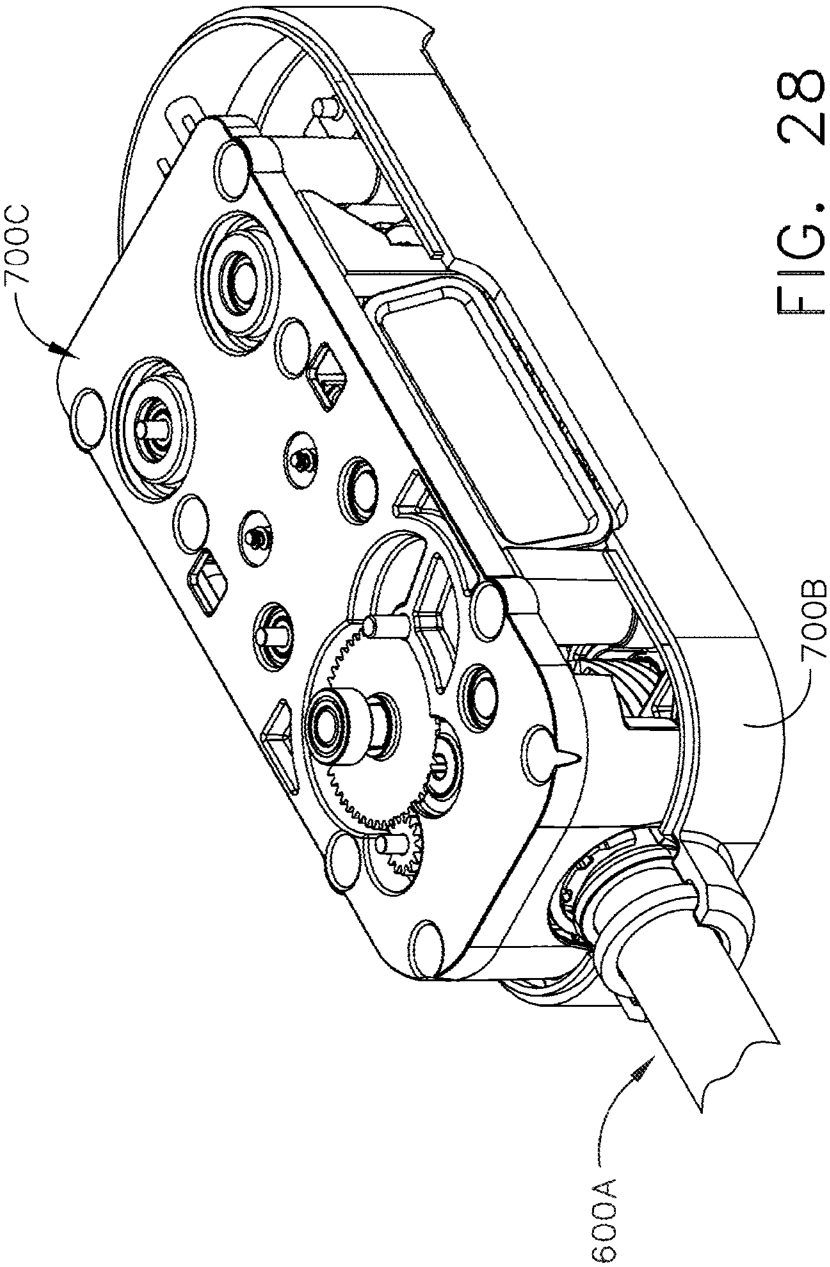
FIG. 28 is a schematic detail view of the housing with an upper shroud thereof removed, in accordance with the disclosed technology.
Figure 29:
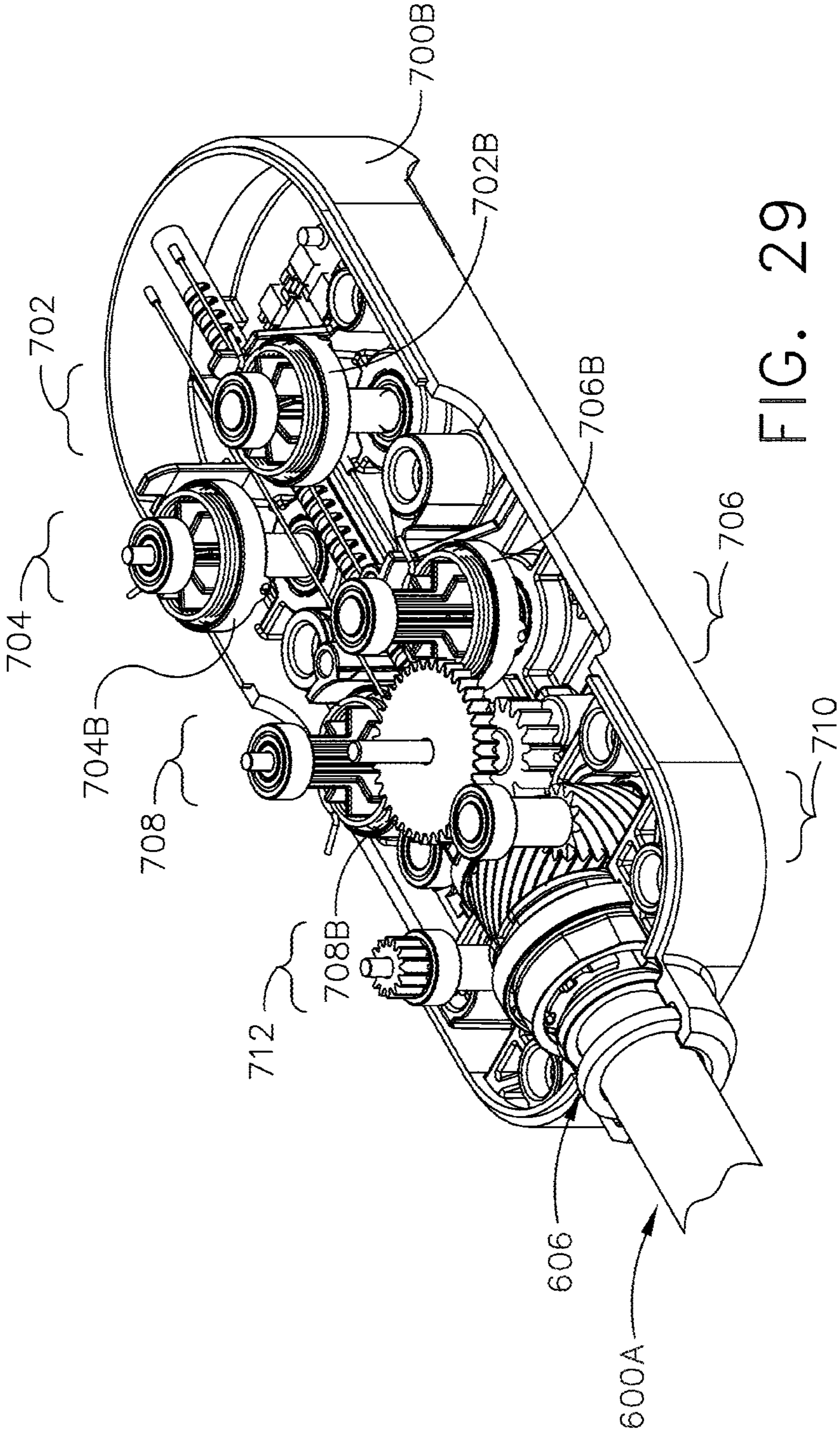
FIG. 29 is a schematic perspective view of the housing with the upper shroud and middle frame thereof removed, in accordance with the disclosed technology.
Figure 30:
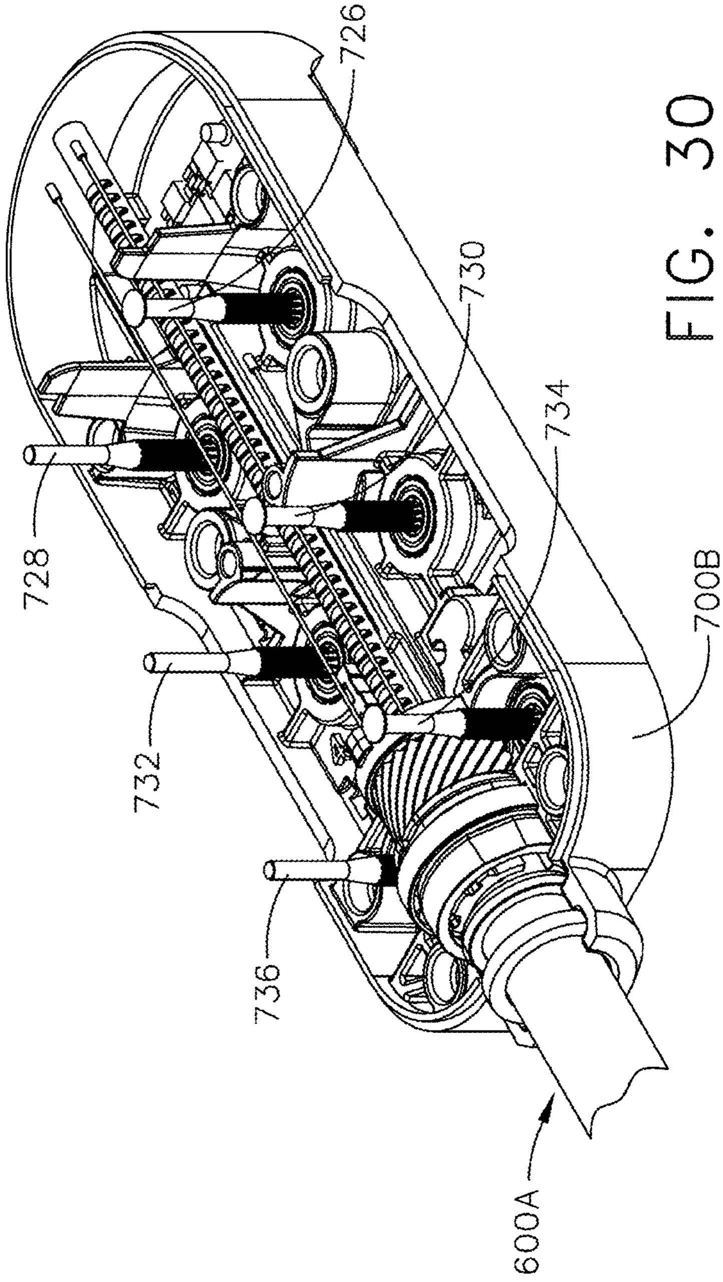
FIG. 30 is a schematic perspective view of the housing with the upper shroud, middle frame thereof removed, and certain subsystem components removed, in accordance with the disclosed technology.
Figure 31:
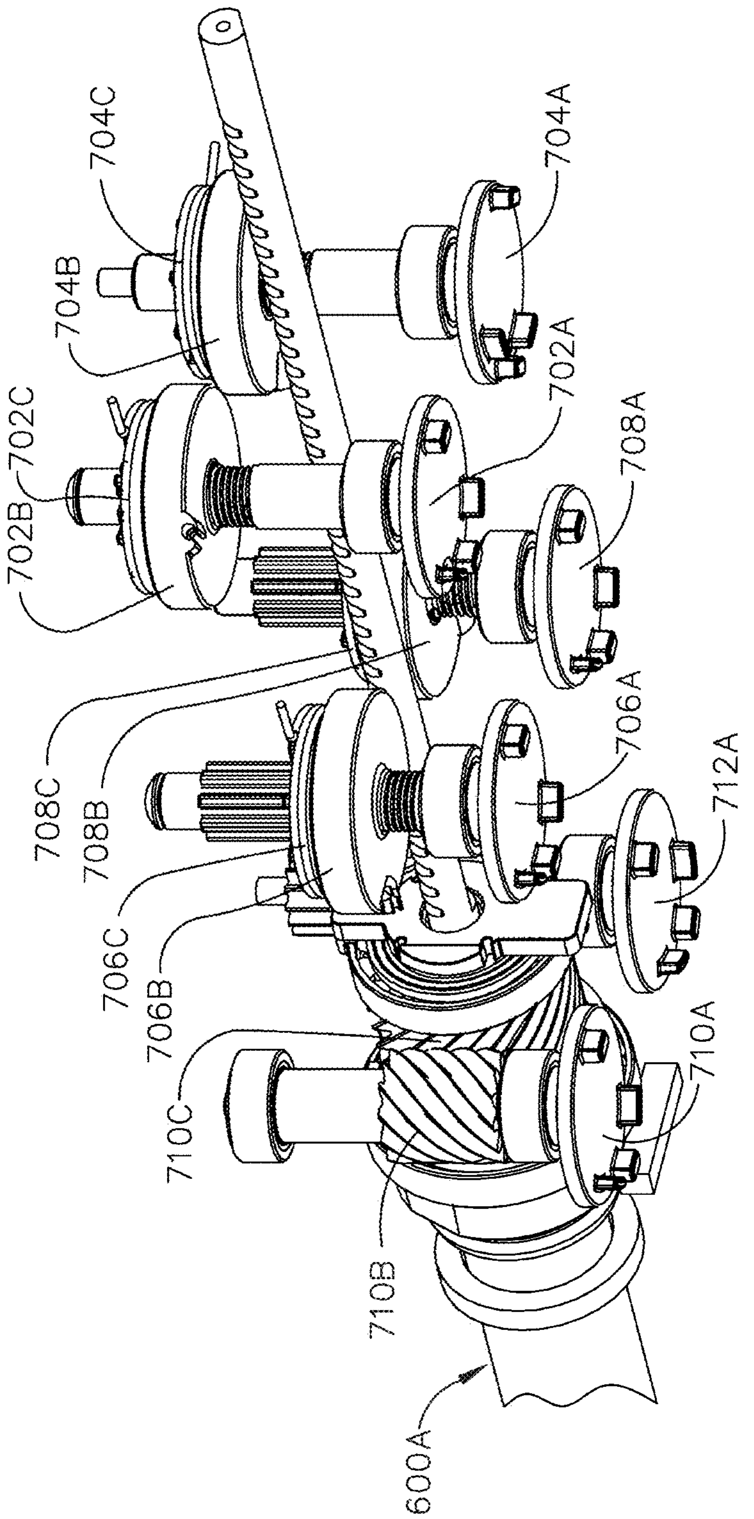
FIG. 31 is a schematic detail view of rotational puck assemblies of the housing, in accordance with the disclosed technology.
Figure 32:
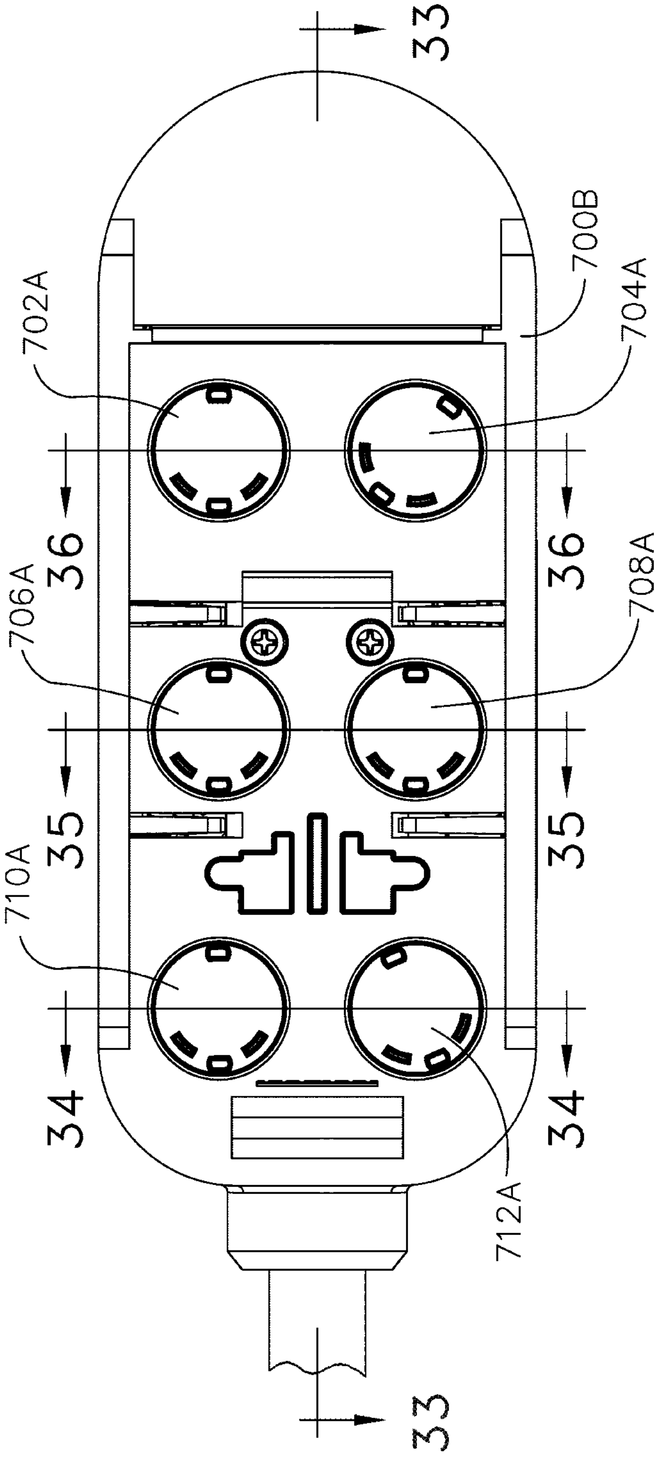
FIG. 32 is a schematic elevation view of the housing, in accordance with the disclosed technology.
Figure 33:
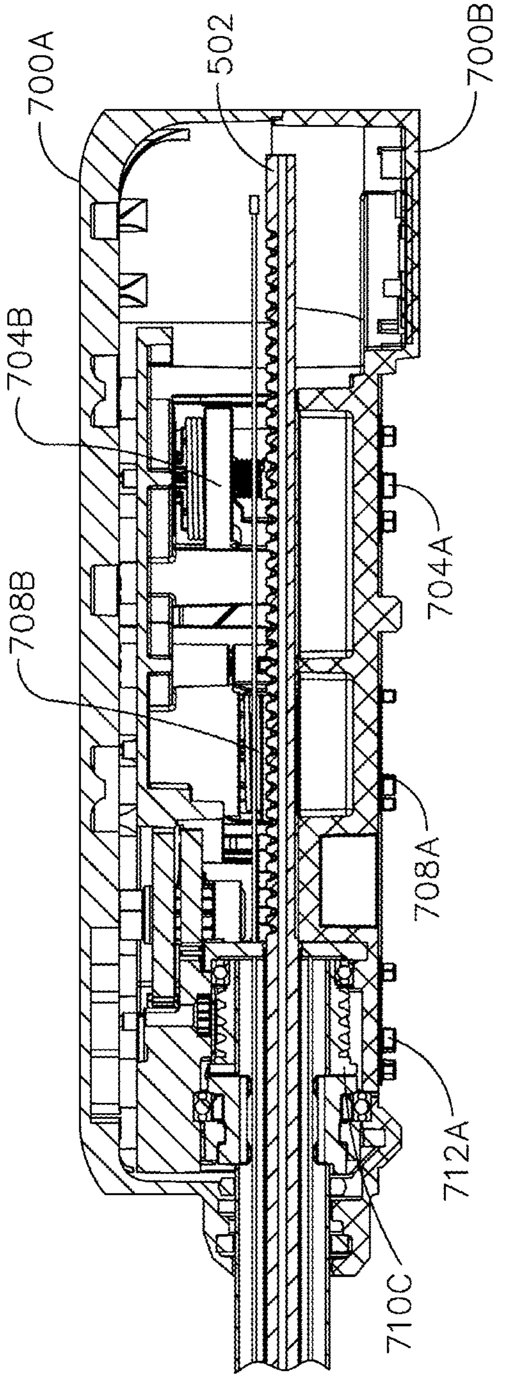
FIG. 33 is a schematic cross-sectional view of the housing, cut relative to line 33-33 in FIG. 32; in accordance with the disclosed technology.
Figure 34:
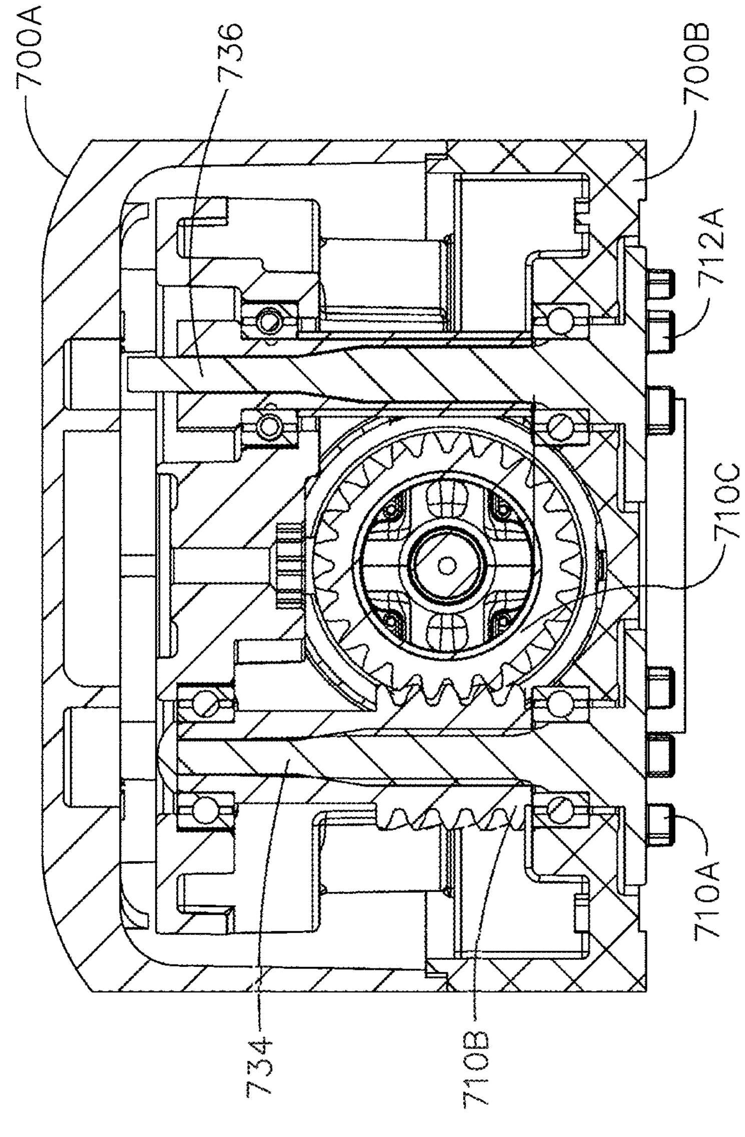
FIG. 34 is a schematic cross-sectional view of the housing, cut relative to line 34-34 in FIG. 32; in accordance with the disclosed technology.

Turning now to the roll subsystem 600, the roll subsystem includes the above-mentioned shaft assembly 600A, rotation joint 606, shaft roll puck assembly 710, which is discussed in greater detail below. As discussed in the foregoing paragraph, the rotatable nature of the differential 520 is also a feature of the roll subsystem. The shaft assembly 600A includes the previously discussed rotatable outer shaft 602 and the inner shaft 604. As shown in the exploded view of FIG. 19, the inner shaft 604 can be split clamshell in design that couple to one another and houses certain components of the surgical instrument 1000, such as the differential 520 and a distal portion of the firing rod 502. Additionally, the clamshell inner shaft 604 can provide support for certain portions of the push coils 508, 510. The inner shaft 604 is fixedly coupled to the outer shaft 602 such that they are rotationally linked. The outer shaft 602 is coupled to the housing via the rotation joint 606, which may include one or more bearings (see, e.g., FIGS. 24 and 27). The bearings engage the housing 700 and permit relative rotation between the outer shaft 604 and the housing 700 upon actuation of the shaft roll puck assembly, which is described in greater detail below. One or both of the shafts 602, 604 are provided with various channels for the cables 402, 404, 406, 408, push rods 504, 506, differential 520, and the like to ride in. Further, a lug is rotationally fixed to the outer shaft and is configured to bottom out with a cavity on the housing to indicate when the outer shaft 602 is in a home position.

VII. Overview of the Housing Puck Assemblies and Integration with the Surgical Instrument Subsystems Turning now primarily to FIGS. 23-35, the housing 700 is configured to engage a robotic platform 2000 controlled by a clinician. To control the aforementioned subsystems 400, 500, 600, respective proximal mechanisms are provided that interface with the robotic platform. More specifically, a housing outer shell, which includes an upper shroud 700A, a lower frame 700B, and a middle frame 700C, houses at least (1) a plurality of articulation puck assemblies 702, 704, 706, 708 for articulation of the end effector 200, (2) a shaft roll puck assembly 710 for rolling the outer shaft 602, (3) a firing puck assembly for translating the knife 206, and (4) a near field radio-frequency identification (RFID) board 724 that communicates information about the surgical instrument 1000 to the robotic platform 2000.

VII. 1. Housing and Articulation Subsystem

Further to the above, the housing includes four articulation puck assemblies 702, 704, 706, 708, provided that four articulation cables 402, 404, 406, 408 are employed in the presently described surgical instrument. A first articulation puck assembly 702 is used cooperatively with the first articulation cable 402. Likewise, the second articulation puck assembly 704 is used cooperatively with the second articulation cable 404, the third articulation puck assembly 706 is used cooperatively with the third articulation cable 406, and the fourth articulation puck assembly 708 is used cooperatively with the first articulation cable 408. In use, the first articulation cable 402 winds on and off the first articulation puck assembly 702, the second articulation cable 404 winds on and off the second articulation puck assembly 704, the third articulation cable 406 winds on and off the third articulation puck assembly 706, and the fourth articulation cable 408 winds on and off the first articulation puck assembly 708.

The first articulation puck assembly 702 includes a first articulation puck 702A, a first capstan 702B, and a first torsion spring 702C. The first articulation puck 702A is provided on an outer face of the lower frame 700B and directly engages the robotic platform 2000. The first capstan 702B is coupled to the first articulation puck 702A and winds the first articulation cable 402 therearound. The first capstan 702B is rotationally affixed to a first pivot pin 726 (which is integral with the first articulation puck 702A). The first capstan 702B is biased by a first torsion spring 702C in a retracting direction to maintain a minimum level of tension in the first articulation cable 402, such as while decoupled from the robotic platform 2000. As the first articulation puck assembly 702 does not include any gearing, the diameter of the first capstan 702B is what dictates the mechanical advantage achieved.

In use, and for example, rotation of the first capstan 702B by the robotic platform 2000, via the first articulation puck 702A, in a first direction winds the first articulation cable 402 around the first capstan 702B, which results in the end effector 200 pivoting upwards and to the left about the articulation joint 300. As discussed earlier, this upwards movement of the end effector 200 is compensated for in the knife firing subsystem by the differential 520. Rotation in the opposite direction by the first articulation puck 702A unwinds the first articulation cable 402 to return the end effector 200 to a position substantially coaxial with the shaft assembly 600A (e.g., coaxial with the roll axis RA).

The second articulation puck assembly 704 includes a second articulation puck 704A, a second capstan 704B, and a second torsion spring 704C. The second articulation puck 704A is provided on an outer face of the lower frame 700B and directly engages the robotic platform 2000. The second capstan 704B is coupled to the second articulation puck 704A and winds the second articulation cable 404 therearound. The second capstan 704B is rotationally affixed to a second pivot pin 728 (which is integral with the second articulation puck 704A). The second capstan 704B is biased by a second torsion spring 704C in a retracting direction to maintain a minimum level of tension in the second articulation cable 404. As the second articulation puck assembly 704 does not include any gearing, the diameter of the second capstan 704B is what dictates the mechanical advantage achieved.

In use, and for example, rotation of the second capstan 704B by the robotic platform 2000, via the second articulation puck 704A, in a first direction winds the second articulation cable 404 around the second capstan 704B, which results in the end effector 200 pivoting upwards and to the right about the articulation joint 300. As discussed earlier, this upwards movement of the end effector 200 is compensated for in the knife firing subsystem by the differential 520. Rotation in the opposite direction by the second articulation puck 704A unwinds the second articulation cable 404 to return the end effector 200 to a position substantially coaxial with the shaft assembly 600A (e.g., coaxial with the roll axis RA).

The third articulation puck assembly 706 includes a third articulation puck 706A, a third capstan 706B, and a third torsion spring 706C. The third articulation puck 706A is provided on an outer face of the lower frame 700B and directly engages the robotic platform 2000. The third capstan 706B is coupled to the third articulation puck 706A and winds the third articulation cable 406 therearound. The third capstan 706B is rotationally affixed to a third pivot pin 730 (which is integral with the third articulation puck 706A). The third capstan 706B is biased by a third torsion spring 706C in a retracting direction to maintain a minimum level of tension in the third articulation cable 406. As the third articulation puck assembly 706 does not include any gearing, the diameter of the third capstan 706B is what dictates the mechanical advantage achieved.

In use, and for example, rotation of the third capstan 706B by the robotic platform 2000, via the third articulation puck 706A, in a first direction winds the third articulation cable 406 around the third capstan 706B, which results in the end effector 200 pivoting downward and to the left about the articulation joint 300. As discussed earlier, this downwards movement of the end effector 200 is compensated for in the knife firing subsystem by the differential 520. Rotation in the opposite direction by the third articulation puck 706A unwinds the third articulation cable 406 to return the end effector 200 to a position substantially coaxial with the shaft assembly 600A (e.g., coaxial with the roll axis RA).

The fourth articulation puck assembly 708 includes a fourth articulation puck 708A, a fourth capstan 708B, and a fourth torsion spring 708C. The fourth articulation puck 708A is provided on an outer face of the lower frame 700B and directly engages the robotic platform 2000. The fourth capstan 708B is coupled to the fourth articulation puck 708A and winds the third articulation cable 408 therearound. The fourth capstan 708B is rotationally affixed to a fourth pivot pin 732 (which is integral with the fourth articulation puck 708A). The fourth capstan 708B is biased by a fourth torsion spring 708C in a retracting direction to maintain a minimum level of tension in the third articulation cable 408. As the fourth articulation puck assembly 708 does not include any gearing, the diameter of the fourth capstan 708B is what dictates the mechanical advantage achieved.

In use, and for example, rotation of the fourth capstan 708B by the robotic platform 2000, via the fourth articulation puck 708A, in a first direction winds the fourth articulation cable 408 around the fourth capstan 708B, which results in the end effector 200 pivoting downwards and to the right about the articulation joint 300. As discussed earlier, this downwards movement of the end effector 200 is compensated for in the knife firing subsystem by the differential 520. Rotation in the opposite direction by the fourth articulation puck 708A unwinds the fourth articulation cable 408 to return the end effector 200 to a position substantially coaxial with the shaft assembly 600A (e.g., coaxial with the roll axis RA).

Of course, and as discussed above, synchronous movement of various combinations of the puck assemblies 702, 704, 706, 708 enables the clinician (via the robotic platform 2000) to position the end effector 200 at any orientation.

Figure 37:
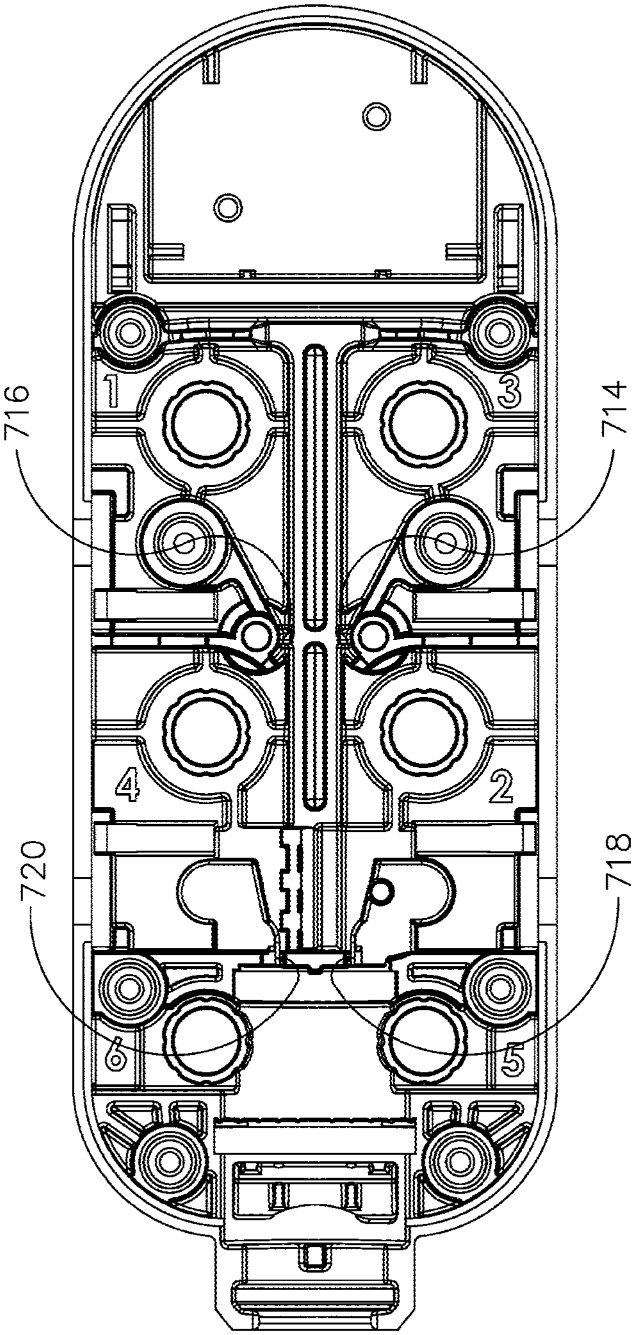
FIG. 37 is a schematic top view of the housing with the upper shroud, middle frame thereof removed, and certain subsystem components removed, in accordance with the disclosed technology.

Additionally, as shown particularly in FIG. 37, the housing 700 (e.g., the lower frame 700B, as shown in FIG. 37) may be provided with a plurality of static redirects 714, 716, 718, 720 that each have a surface that engages a respective articulation cable 402, 404, 406, 408 to redirect it within the housing 700. These redirects 714, 716, 718, 720 ensure proper routing of the articulation cables 402, 404, 406, 408.

VII. 2. Housing and Roll Subsystem

Further to the above, the shaft roll puck assembly 710 includes a shaft roll puck 710A, a first screw gear 710B, and a second screw gear 710C. The shaft roll puck 710A is provided on an outer face of the lower frame 700B, is integral with a fifth pivot pin 734, and directly engages the robotic platform 2000. The first screw gear 710B is coaxial with and rotatable with the shaft roll puck 710A. The second screw gear 710C is meshed with the first screw gear 710B and coupled with the rotatable outer shaft 602.

In use, and for example, rotation of the first screw gear 710B by the robotic platform 2000, via the shaft roll puck 710A, in a first direction turns the second screw gear 710C to roll the outer shaft 602 (e.g., in a clockwise direction about the roll axis RA), as discussed in greater detail above. Rotation of the first screw gear in an opposite second direction causes the outer shaft 602 to roll in an opposite direction (e.g., a counterclockwise direction about the roll axis RA).

VII. 3. Housing and Firing Subsystem

Further to the above, the firing puck assembly includes a firing puck 712A, a drive gear 712A1, a geartrain 712B, and a driven gear or pinion 712C. The firing puck 712A is provided on an outer face of the lower frame 700B, is integral with a sixth pivot pin 736, and directly engages the robotic platform 2000. The drive gear 712A1 directly rotates with the firing puck 712A. As particularly shown in FIG. 23, the geartrain 712B is rotatable with the firing puck 712A and the drive gear 712A1. In some embodiments, the geartrain 712B includes a first idler gear 712B1 meshed with the drive gear 712A1, a second idler gear 712B2 coaxial with and rotationally affixed to the first idler gear 712B1, and a third idler gear 712B3 meshed with the second idler gear 712B2. The pinion 712C is coaxial with and rotationally affixed to the third idler gear 712B3. Further, the pinion 712C meshes with the rack 530 of the firing rod 502 to effect translational movement thereof (to fire and retract the knife 206, as discussed above).

In use, and for example, rotation of the firing puck 712A by the robotic platform 2000 causes rotation of the drive gear 712A1, which in turn drives the geartrain 712B to rotate the pinion 712C. Depending on the direction of rotation of the firing puck 712A, the firing rod 502 is either moved in a distal direction (i.e., towards the end effector 200) to close the anvil 204 and/or fire the knife 206 or a proximal direction (i.e., towards a rear of the housing 700) to retract the knife 206 and/or open the anvil 204.

IX. Clauses

The disclosed technology described herein can be further understood according to the following clauses:

Clause 1. An end effector (200) for a surgical instrument (1000) comprising: a jaw (202); an anvil (204) coupled to the jaw (202) and movable between an open position, a grasping position, and a clamping position; and a knife (206) slidably coupled to the anvil (204) to move the anvil (204) between the open position, the grasping position, and the clamping position.

Clause 2. The end effector (200) of clause 1, wherein the jaw (202) defines an elongated channel (208) for receiving a staple cartridge (210).

Clause 3. The end effector (200) of any one of clauses 1-2, further comprising a pivot pin (212) spaced from the knife (206) and extending through the anvil (204) and the jaw (202), the pivot pin (212) pivotally coupling the jaw (202) and the anvil (204).

Clause 4. The end effector (200) of any one of clauses 1-3, wherein the anvil (204) has an anvil proximal end (204A) and an anvil distal end (204B), the anvil proximal end (204A) defining an anvil ramp surface (216) that the knife (206) slidably engages to move the anvil between the open position, the grasping position, and the clamping position.

Clause 5. The end effector (200) of clause 4, wherein the anvil ramp surface (216) (i) is upwardly sloped at a first angle (218) and (ii) arcuately tapers, in a distal direction, to a substantially horizontal second angle (220).

Clause 6. The end effector (200) of clause 4, wherein the ramp surface (216) comprises a single radius curve, a series of multi-radius curves, a series of multi-radius curves with a series of inflection points, and/or a linearly slope.

Clause 7. The end effector (200) of any one of clauses 4-6, wherein the anvil proximal end (204A) further defines a laterally extending kidney bean-shaped opening (222), the anvil ramp surface (216) forming a lower surface of the kidney bean-shaped opening (222).

Clause 8. The end effector of clause 7a, wherein the kidney bean-shaped opening is open at lateral ends (222A, 222B) thereof.

Clause 9. The end effector (200) of any one of clauses 1-8, wherein the anvil (204) defines a longitudinally extending upper knife channel (224) in which the knife (206) slidably rides to move the anvil (204) between the open position, the grasping position, and the clamping position.

Clause 10. The end effector (200) of clause 9, wherein the upper knife channel (224) comprises (i) a centrally disposed cylindrical upper knife channel portion (226) and (ii) at least one lateral upper knife channel wing (228) that extends away from the upper knife channel portion (226).

Clause 11. The end effector (200) of any one of clauses 1-10, wherein the jaw (202) or a staple cartridge (210) defines a longitudinally extending lower knife channel (230) in which the knife slidably rides when the anvil (204) moves between the open position, the grasping position, and the clamping position.

Clause 12. The end effector (200) of clause 11, wherein the lower knife channel (230) comprises (i) a centrally disposed cylindrical lower knife channel portion (232) and (ii) at least one lateral lower knife channel wing (234) that extends away from the lower knife channel portion.

Clause 13. The end effector (200) of any one of clauses 1-12, wherein the knife (206) comprises a knife sled (236) that comprises an upper knife tab (238), the upper knife tab (238) further comprising (i) a centrally disposed cylindrical upper knife tab portion (240) and (ii) at least one upper knife tab lateral wing (242) that extends away from the upper knife tab portion (240).

Clause 14. The end effector (200) of clause 13, wherein the upper knife tab portion (240) defines an upper knife tab opening (244) configured to receive a first center cable (512).

Clause 15. The end effector (200) of any one of clauses 13-14, wherein the lateral wing (242) comprises an angled surface (242A) that is configured to slidably ride on the anvil ramp surface (216) when the anvil (204) moves between the open position, the grasping position, and the clamping position.

Clause 16. The end effector (200) of any one of clauses 13-15, wherein the upper knife tab portion (240) is configured to slidably ride in the upper knife channel portion (226) and the at least one upper knife tab lateral wing (242) is configured to slidably ride in the at least one lateral upper knife channel wing (228).

Clause 17. The end effector of any one of clauses 1-16, wherein the knife (206) comprises a knife sled (236) that comprises a lower knife tab (246), the lower knife tab (246) further comprising (i) a centrally disposed cylindrical lower knife tab portion (248) and (ii) at least one lower knife tab lateral wing (250) that extends away from the lower knife tab portion (248).

Clause 18. The end effector of clause 17, wherein the lower knife tab portion (248) defines a lower knife tab opening (252) configured to receive a second center cable (514).

Clause 19. The end effector of any one of clauses 17-18, wherein the lower knife tab portion (248) is configured to slidably ride in the lower knife channel portion (232) and the at least one lower knife tab lateral wing (248) is configured to slidably ride in the at least one lateral lower knife channel wing (234).

Clause 20. The end effector of any one of clauses 1-19, wherein the jaw (202) comprises: a knife channel (230) defined in a longitudinal direction of the jaw (202); and a cleanout port (202A) defined in a transverse direction of the jaw (202) and proximate a distal end of the jaw (202), the cleanout port (202A) extending through a bottommost surface of the jaw (202) and connecting with the knife channel (230).

Clause 21. The end effector of clause 20, wherein the jaw (202) comprises: a hard stop (230A) mounted in the knife channel (230), the hard stop (230A) partially overlapping with the cleanout port (202A) in the longitudinal direction.

Clause 22. The end effector of any one of clauses 1-2 and 9-21, further comprising a pivot pin (212A) pivotally coupling the jaw (202) and the anvil (204), wherein the anvil (204) has an anvil proximal end (204A) and an anvil distal end (204B), the anvil proximal end (204A) defining an anvil ramp surface (216) that the knife (206) slidably engages to move the anvil between the open position, the grasping position, and the clamping position, and a lowermost point of the anvil ramp surface (216) is spaced a predetermined distance (D1) from the pivot pin 212A along a vertical direction (V) of the end effector (200).

The embodiments described above are cited by way of example, and the present invention is not limited by what has been particularly shown and described hereinabove. Rather, the scope of the invention includes both combinations and sub combinations of the various features described and illustrated hereinabove, as well as variations and modifications thereof which would occur to persons skilled in the art upon reading the foregoing description and which are not disclosed in the prior art.

What is claimed is:

1. An end effector for a surgical instrument comprising:

a jaw;

an anvil coupled to the jaw and movable between an open position, a grasping position, and a clamping position, the anvil comprising an anvil proximal end and an anvil distal end, the anvil proximal end defining an anvil ramp surface, and the anvil proximal end defining a laterally extending kidney bean-shaped opening, with the anvil ramp surface forming a lower surface of the kidney bean-shaped opening; and a knife that slidably engages the anvil ramp surface to move the anvil between the open position, the grasping position, and the clamping position.

2. The end effector of claim 1, wherein the jaw defines an elongated channel for receiving a staple cartridge.

3. The end effector of claim 1, further comprising a pivot pin spaced from the knife and extending through the anvil and the jaw, the pivot pin pivotally coupling the jaw and the anvil.

4. The end effector of claim 1, wherein the anvil ramp surface (i) is upwardly sloped at a first angle and (ii) arcuately tapers, in a distal direction, to a substantially horizontal second angle.

5. The end effector of claim 1, wherein the anvil ramp surface comprises a single radius curve, a series of multi-radius curves, a series of multi-radius curves with a series of inflection points, and/or a linear slope.

6. The end effector of claim 1, wherein the kidney bean-shaped opening is open at lateral ends thereof.

7. The end effector of claim 1, wherein the anvil defines a longitudinally extending upper knife channel in which the knife slidably rides to move the anvil between the open position, the grasping position, and the clamping position.

8. The end effector of claim 7, wherein the upper knife channel comprises (i) a centrally disposed cylindrical upper knife channel portion and (ii) at least one lateral upper knife channel wing that extends away from the upper knife channel portion.

9. The end effector of claim 1, wherein the knife comprises a knife sled that comprises an upper knife tab, the upper knife tab further comprising (i) a centrally disposed cylindrical upper knife tab portion and (ii) at least one upper knife tab lateral wing that extends away from the upper knife tab portion.

10. The end effector of claim 9, wherein the upper knife tab portion defines an upper knife tab opening configured to receive a first center cable.

11. The end effector of claim 9, wherein the at least one upper knife tab lateral wing comprises an angled surface that is configured to slidably ride on the anvil ramp surface when the anvil moves between the open position, the grasping position, and the clamping position.

12. The end effector of claim 9, wherein the anvil defines a longitudinally extending upper knife channel, wherein the upper knife channel comprises (i) an upper knife channel portion and (ii) at least one lateral upper knife channel wing, and wherein the upper knife tab portion is configured to slidably ride in the upper knife channel portion and the at least one upper knife tab lateral wing is configured to slidably ride in the at least one lateral upper knife channel wing.

13. The end effector of claim 1, wherein the knife comprises a knife sled that comprises a lower knife tab, the lower knife tab further comprising (i) a centrally disposed cylindrical lower knife tab portion and (ii) at least one lower knife tab lateral wing that extends away from the lower knife tab portion.

14. The end effector of claim 13, wherein the lower knife tab portion defines a lower knife tab opening configured to receive a second center cable.

15. The end effector of claim 13, wherein the jaw defines a longitudinally extending lower knife channel, wherein the lower knife channel comprises (i) a lower knife channel portion and (ii) at least one lateral lower knife channel wing, and wherein the lower knife tab portion is configured to slidably ride in the lower knife channel portion and the at least one lower knife tab lateral wing is configured to slidably ride in the at least one lateral lower knife channel wing.

16. The end effector of claim 1, wherein the jaw comprises:

a knife channel defined in a longitudinal direction of the jaw; and a cleanout port defined in a transverse direction of the jaw and proximate a distal end of the jaw, the cleanout port extending through a bottommost surface of the jaw and connecting with the knife channel.

17. The end effector of claim 1, wherein the jaw or a staple cartridge defines a longitudinally extending lower knife channel in which the knife slidably rides when the anvil moves between the open position, the grasping position, and the clamping position.

18. The end effector of claim 17, wherein the lower knife channel comprises (i) a centrally disposed cylindrical lower knife channel portion and (ii) at least one lateral lower knife channel wing that extends away from the lower knife channel portion.

19. An end effector for a surgical instrument comprising:

a jaw;

an anvil coupled to the jaw and movable between an open position, a grasping position, and a clamping position, the anvil defining an anvil ramp surface; and a knife slidably coupled to the anvil to move the anvil between the open position, the grasping position, and the clamping position, the knife comprising a knife sled that comprises an upper knife tab, the upper knife tab further comprising (i) a centrally disposed cylindrical upper knife tab portion and (ii) at least one upper knife tab lateral wing that extends away from the upper knife tab portion, the at least one upper knife tab lateral wing comprising an angled surface that is configured to slidably ride on the anvil ramp surface when the anvil moves between the open position, the grasping position, and the clamping position.

* * * * *